(12) United States Patent  
Mazar

(10) Patent No.: US 8,903,484 B2
(45) Date of Patent: Dec. 2, 2014

(54) METHOD AND APPARATUS TO MEASURE BIOELECTRIC IMPEDANCE OF PATIENT TISSUE

(71) Applicant: Corventis, Inc., St. Paul, MN (US)

(72) Inventor: Scott T. Mazar, Woodbury, MN (US)

(73) Assignee: Corventis, Inc., Saint Paul, MN (US)

( * ) Notice: Subject to any disclaimer, the term of this patent is extended or adjusted under 35 U.S.C. 154(b) by 0 days.

(21) Appl. No.: 13/850,678

(22) Filed: Mar. 26, 2013

(65) Prior Publication Data

US 2014/0012154 A1    Jan. 9, 2014

Related U.S. Application Data

(63) Continuation of application No. 12/426,497, filed on Apr. 20, 2009, now Pat. No. 8,412,317.

(60) Provisional application No. 61/046,221, filed on Apr. 18, 2008.

(51) Int. Cl.
*A61B 5/00* (2006.01)

(52) U.S. Cl.
USPC .......................................................... 600/547

(58) Field of Classification Search
USPC ......... 600/372, 382, 384, 386, 391, 393, 394, 600/547
See application file for complete search history.

(56) References Cited

U.S. PATENT DOCUMENTS

| | | | |
|---|---|---|---|
| 4,674,511 A | 6/1987 | Cartmell | |
| 5,406,945 A | 4/1995 | Riazzi et al. | |
| 6,546,285 B1 | 4/2003 | Owen et al. | |
| 6,643,541 B2 | 11/2003 | Mok et al. | |
| 7,273,454 B2 | 9/2007 | Raymond et al. | |
| 7,515,043 B2 | 4/2009 | Welch et al. | |
| 8,235,949 B2* | 8/2012 | Hack et al. | 604/180 |
| 2002/0022786 A1 | 2/2002 | Takehara et al. | |
| 2002/0180605 A1 | 12/2002 | Ozguz et al. | |
| 2003/0069510 A1 | 4/2003 | Semler | |
| 2005/0251004 A1 | 11/2005 | Istvan et al. | |

(Continued)

OTHER PUBLICATIONS

Scapa Medical product listing and descriptions (2008) available at http://www.caapana.com/productlist.jsp and http://www.metplus.co.rs/pdf/prospekti/Samolepljivemedicinsketrake.pdf; retrieved via WayBack Machine Aug. 29, 2013.

*Primary Examiner* — Max Hindenburg
(74) *Attorney, Agent, or Firm* — Billion & Armitage

(57) ABSTRACT

A device to measure tissue impedance comprises drive circuitry coupled to calibration circuitry, such that a calibration signal from the calibration circuitry corresponds to the current delivered through the tissue. Measurement circuitry can be coupled to measurement electrodes and the calibration circuitry, such that the tissue impedance can be determined in response to the measured calibration signal from the calibration circuitry and the measured tissue impedance signal from the measurement electrodes. Processor circuitry comprising a tangible medium can be configured to determine a complex tissue impedance in response to the calibration signal and the tissue impedance signal. The processor can be configured to select a frequency for the drive current, and the amount of drive current at increased frequencies may exceed a safety threshold for the drive current at lower frequencies.

21 Claims, 15 Drawing Sheets

(56) References Cited

U.S. PATENT DOCUMENTS

| | | |
|---|---|---|
| 2006/0238333 A1 | 10/2006 | Welch et al. |
| 2007/0069887 A1 | 3/2007 | Welch et al. |
| 2007/0208232 A1 | 9/2007 | Kovacs |
| 2008/0139953 A1 | 6/2008 | Baker et al. |
| 2009/0132018 A1 | 5/2009 | DiUbaldi et al. |
| 2010/0063365 A1 | 3/2010 | Pisani et al. |
| 2010/0081913 A1 | 4/2010 | Cross et al. |
| 2012/0310070 A1 | 12/2012 | Kumar et al. |

* cited by examiner

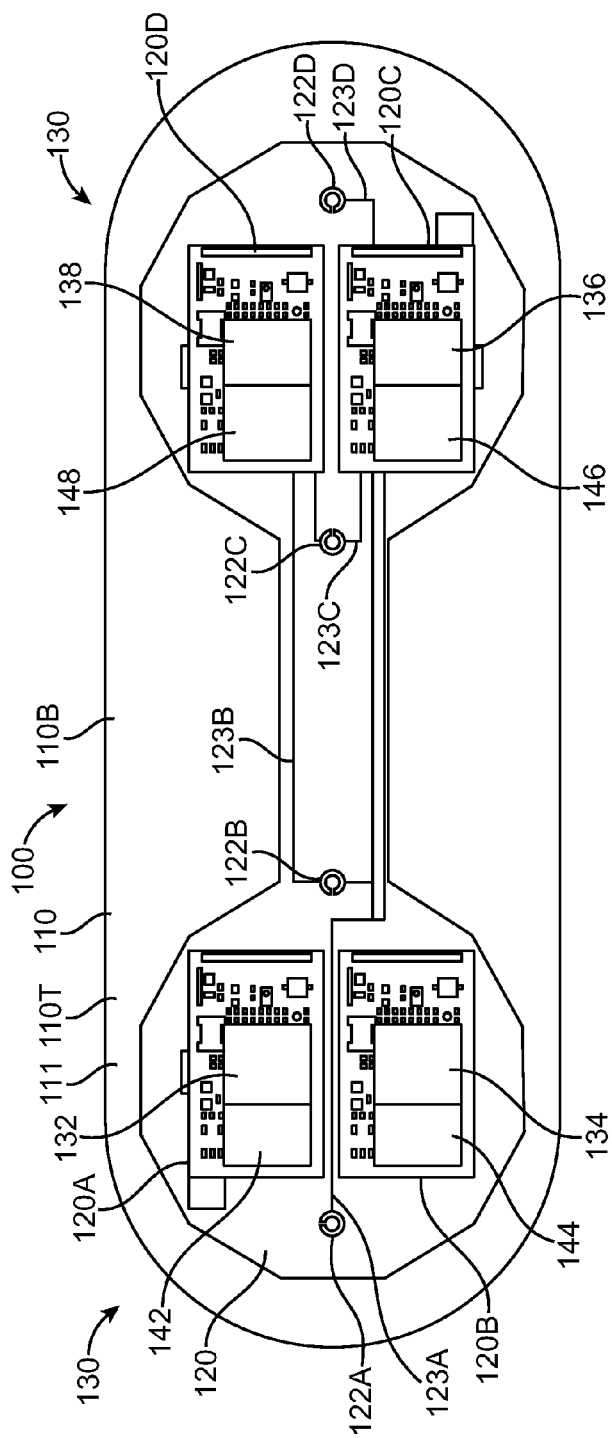
FIG. 1D
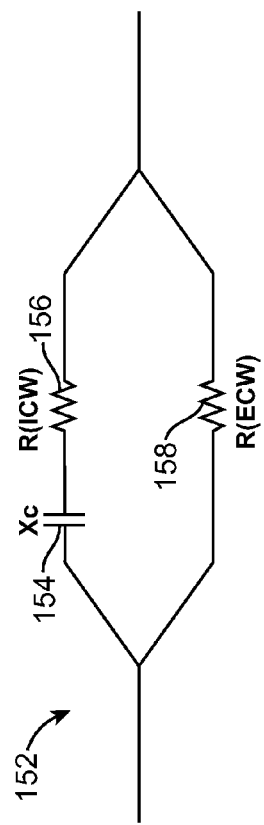
FIG. 1D1

METHOD AND APPARATUS TO MEASURE BIOELECTRIC IMPEDANCE OF PATIENT TISSUE

CROSS-REFERENCES TO RELATED APPLICATIONS

This application is a continuation of U.S. patent application Ser. No. 12/426,497 filed Apr. 20, 2009 and titled "Method and Apparatus to Measure Bioelectric Impedance of Patient Tissue", now U.S. Pat. No. 8,412,317, which claims the benefit under 35 USC 119(e) of U.S. Provisional Application No. 61/046,221 filed Apr. 18, 2008; the full disclosures of which are incorporated herein by reference in its entirety.

BACKGROUND OF THE INVENTION

The present invention relates to patient monitoring. Although embodiments make specific reference to monitoring impedance and electrocardiogram signals with an adherent patch, the system methods and device described herein may be applicable to many applications in which physiological monitoring is used, for example physiological monitoring with implantable devices.

Patients are often treated for diseases and/or conditions associated with a compromised status of the patient, for example a compromised physiologic status. In some instances, a patient may report symptoms that require diagnosis to determine the underlying cause. For example, a patient may report fainting or dizziness that requires diagnosis, in which long term monitoring of the patient can provide useful information as to the physiologic status of the patient. In some instances a patient may have suffered a heart attack and require care and/or monitoring after release from the hospital. One example of a device to provide long term monitoring of a patient is the Holter monitor, or ambulatory electrocardiography device. In addition to measuring heart signals with electrocardiograms, known physiologic measurements include impedance measurements that can be used to assess the status of the patient.

Impedance measurements can be used to measure hydration and respiration of a patient. Long term impedance measurements used to determine patient hydration in relation to cardiac status represents one area where impedance measurements may be useful. Although current methodologies have been somewhat successful in measuring hydration, work in relation to embodiments of the present invention suggests that known methods and apparatus for monitoring patient hydration with impedance may be less than ideal. Some current devices may not accurately measure the impedance of the internal tissue of the patient, thereby making accurate hydration measurements more difficult. In some instances, the skin of the patient and/or coupling of electrodes to the skin may affect the impedance measurements. For example, environmental factors external to the patient may effect the measurements, for example when the patient showers. The electronics used to measure complex impedance signals of the patient may be somewhat larger than ideal and may not provide as much accuracy as would be ideal. Thus, devices that are worn by the patient may be somewhat uncomfortable, which may lead to patients not wearing the devices and not complying with direction from the health care provider, such that data collected may be less than ideal. As a compromise to reduce size and improve patient comfort, some devices to measure impedance may use circuitry that measures part of the tissue impedance without determining the resistance and reactance components of the complex impedance of the tissue.

Although implantable devices may be used in some instances, many of these devices can be invasive and/or costly, and may suffer at least some of the shortcomings of known wearable devices described above. In addition, implantable devices can be invasive and/or costly such that many patients cannot receive a therapeutic benefit. Although injectable devices may decrease invasiveness, the size requirements of injectable devices can place limitations on the circuitry and may limit the accuracy of such devices.

Therefore, a need exists for improved patient monitoring with impedance measurements. Ideally, such improved patient monitoring would avoid at least some of the shortcomings of the present methods and devices.

BRIEF SUMMARY OF THE INVENTION

The present invention relates to patient monitoring. Although embodiments make specific reference to monitoring impedance and electrocardiogram signals with an adherent patch, the system methods and device described herein may be applicable to many applications in which physiological monitoring with impedance measurements are used, for example physiological monitoring with implantable devices.

In many embodiments of the present invention, tissue impedance is determined in response a calibration signal from calibration circuitry and a tissue impedance signal from the tissue. Because the tissue impedance can be determined from both a tissue impedance signal and a calibration signal, errors can be minimized, for example errors that correspond to fluctuations in drive current, variations in measurement circuitry gain, time delays of the drive circuitry, time delays of the measurement circuitry, and parasitic impedance of the tissue, for example skin. The drive circuitry can be coupled to the calibration circuitry and at least two drive electrodes so as to drive current through the tissue and the calibration circuitry. Thus, a calibration signal from the calibration circuitry can be measured when the electrodes are connected to the patient, such that the calibration signal substantially corresponds to the current actually delivered through the tissue. Measurement circuitry can be connected to at least two measurement electrodes so as to measure a tissue impedance signal in response to the impedance of the tissue and the current through the tissue. The measurement circuitry can also be coupled to the calibration circuitry to measure the calibration signal, such that the tissue impedance can be determined in response to the measured calibration signal and the measured tissue impedance signal. Processor circuitry comprising a tangible medium can be configured to determine a complex tissue impedance in response to the calibration signal and the tissue impedance signal, such errors are minimized which correspond to fluctuations in drive current, variations in measurement circuitry gain, time delays of the drive circuitry, time delays of the measurement circuitry, and parasitic impedance of the tissue. As the calibration resistor can be provided with the drive circuitry and measurement circuitry, the system can be self calibrating, thereby eliminating a time consuming step at manufacture and minimizing memory resources of the controlling computer and/or processor. In many embodiments, the processor can be configured to select a frequency for the drive current, and the drive circuitry can be configured to increase the amount of drive current with increasing frequency, such that the signal to noise ratio can be improved. The amount of drive current at a selected increased frequency may even exceed a safety threshold for the amount of drive current at a lower frequency. The measurement circuitry can be configured to decrease the gain of the impedance signal with increasing frequency, such that the increased amount of current does not saturated the measurement circuitry and/or digitization electronics such as an analog to digital converter.

In a first aspect, embodiments of the present invention provide a device for measuring an impedance of a tissue of a patient. The calibration circuitry comprises an impedance. At least four electrodes are configured to couple to the tissue of the patient. The at least four electrodes may comprise at least two measurement electrodes and at least two drive electrodes. Drive circuitry is coupled to the at least two drive electrodes and the calibration circuitry to pass a current through the at least two drive electrodes and the calibration circuitry. Measurement circuitry is configured to couple to the at least two measurement electrodes and the calibration circuitry, such that the measurement circuitry can be configured to measure a calibration signal from the calibration circuitry and a tissue impedance signal from the at least two measurement electrodes. Processor circuitry comprising a tangible medium is configured to determine the impedance of the tissue in response to the calibration signal and the tissue impedance signal.

In many embodiments, the processor circuitry comprises as least one of an impedance converter or a microcontroller. The processor circuitry can be configured to determine the impedance of the tissue with a discrete Fourier transform of at least one of measurement signal or the current signal.

In many embodiments, the calibration circuitry can be connected in series between the drive circuitry and the at least two measurement electrodes to calibrate the tissue impedance measurement when the at least two electrodes are connected to the patient. The drive circuitry can be configured to pass the current through the tissue and the calibration circuitry to generate the tissue measurement signal and the calibration signal when the at least four electrodes are connected to the tissue. The calibration circuitry may comprise a calibration resistor, and the measurement circuitry can be configured to measure the calibration signal in response to the current through the calibration resistor and the tissue. The measurement circuitry can be configured to measure the tissue measurement signal in response to the current through the tissue and the calibration resistor. The processor can be configured to determine the tissue impedance from the calibration signal and the tissue measurement signal.

In many embodiments, at least one switch is coupled to the drive circuitry, the measurement circuitry, the calibration circuitry and the at least four electrodes. The at least one switch comprises a first configuration and a second configuration, In the first configuration the at least one switch couples the measurement circuitry to the calibration circuitry to measure the calibration signal. In the second configuration the at least one switch couples the measurement circuitry to the at least two measurement electrodes to measure the tissue impedance signal. The processor circuitry can be coupled to the at least one switch to select the first configuration or the second configuration.

In many embodiments, the measurement circuitry comprises a first measurement circuit configured to measure the calibration signal and a second measurement circuit configured to measure the tissue impedance signal.

In many embodiments, the calibration circuitry comprises at least one resistor connected in series to the drive circuitry and the at least two drive electrodes, such that a resistance of the resistor corresponds to at least 90% the impedance of the calibration circuitry. The calibration circuitry may comprise a resistance, and the calibration signal may comprise a complex calibration signal. The tissue impedance signal may comprise a complex tissue impedance signal, and the processor can be configured to determine a complex impedance of the tissue in response to the complex calibration signal and the complex tissue impedance signal.

In many embodiments, the processor is configured to store a calibration value comprising a resistance of the calibration circuitry that corresponds to a real number, and the calibration signal corresponds to the resistance of the calibration circuitry, delays of the drive circuitry and delays of the measurement circuitry. The processor can be configured to determine a complex calibration coefficient in response to the calibration value and the calibration signal. The tissue impedance may comprise a complex tissue impedance and processor can be configured to determine the complex tissue impedance in response to the complex calibration coefficient and the tissue impedance signal. For example, the processor can be configured to determine a complex tissue parameter from the tissue impedance signal, and the processor can be configured to determine the complex tissue impedance with at least one of a complex multiplication or a complex division of the complex calibration coefficient and the complex tissue parameter. The processor can be configured to determine the complex tissue parameter with a discrete Fourier transform of the tissue impedance signal and determine the complex calibration coefficient with a discrete Fourier transform of the calibration signal. The delays of the drive circuitry and the measurement circuitry can correspond to a phase angle of the calibration signal of at least about 90 degrees.

In many embodiments, the processor is configured to select a first frequency and a second frequency to measure impedance signals of the calibration circuitry at each of the first frequency and the second frequency, and the processor is configured to measure impedance signals of the tissue at each of the first frequency and the second frequency. The processor can be configured to determine an impedance of the tissue at the each of the first frequency and the second frequency in response to the impedance signals of the calibration circuitry measured at each of the first frequency and the second frequency and the impedance signals of the tissue measured at each of the first frequency and the second frequency.

In many embodiments, the processor is configured to store a tolerance range and measure the calibration circuitry in response to the impedance signal of the tissue and the tolerance range. The tolerance range may comprise plus or minus twenty percent of a baseline tissue impedance measurement, and the processor can be configured to measure the calibration circuitry in response to the tissue impedance outside the tolerance range.

In another aspect, embodiments of the present invention provide a device for measuring an impedance of a tissue of a patient. The device comprises at least four electrodes configured to couple to the tissue of the patient. The at least four electrodes comprising at least two drive electrodes, and at least two measurement electrodes. Drive circuitry is coupled to the at least two drive electrodes to pass a variable current through the tissue to generate a tissue measurement signal. The drive circuitry is configured to increase the current from a first current amount at a first frequency to a second current amount at a second frequency, in which the second frequency greater than the first frequency. Measurement circuitry is coupled to the at least two measurement electrodes to determine the impedance of the tissue in response to the tissue measurement signal. The measurement circuitry comprises a variable gain of the measurement signal, and the variable gain is configured to decrease from a first gain at the first frequency to a second gain at the second frequency.

In many embodiments, the variable current of the drive circuitry comprises a drive current frequency response, and the variable gain of the measurement circuitry comprises variable gain frequency response, in which the variable gain frequency response comprises an inverse of the drive current frequency response.

In many embodiments, the drive circuitry is configured to increase the second current amount to at least four times the first current amount, and the measurement circuitry is configured to decrease the second gain to no more than about one half of the first gain. In specific embodiments, the drive circuitry is configured to increase the second current amount to at least ten times the first current amount, and the measurement circuitry is configured to decrease the second gain to no more than about one third of the first gain.

In many embodiments, the second frequency is at least 1 kHz, and the second current amount is at least 10 μA and no more than 1000 μA. The first frequency corresponds to a first safety threshold of the first current, and the second frequency corresponds to a second safety threshold of the second current. The drive circuitry can be configured to exceed the first safety threshold with the second current amount and not to exceed the second safety threshold with the second current amount. The drive circuitry can be configured to exceed the first safety threshold with the second current by at least a factor of two. The safety threshold of the first current may correspond to 10 μA or a product of the first current in μA times the first frequency in kHz, whichever is greater.

In another aspect, embodiments of the present invention provide a method of measuring patient impedance. The method comprises providing at least four electrodes comprising at least two drive electrodes and at least two measurement electrodes. The at least two drive electrodes can be connected in series to a calibration resistor. Measurement circuitry is provided to measure a tissue impedance signal from the measurement electrodes. A drive current is passed through the at least two drive electrodes and the calibration resistor with drive circuitry. A current signal is measured from the calibration resistor in response to the current through the calibration resistor. The tissue impedance signal is measured from the measurement electrodes. The tissue impedance is determined in response to the current signal and the tissue impedance signal.

In many embodiments, the current signal from the calibration resistor is measured with the measurement circuitry.

In many embodiments, the tissue impedance can be determined with an impedance converter. The current signal from the calibration resistor may comprise a first voltage that is converted into a first current and the first current can be fed into the impedance converter. The tissue impedance signal from the measurement electrodes may comprise a second voltage that can be converted to a second current and the second current fed into the impedance converter.

In many embodiments, the drive circuitry may comprise a network to limit the drive current through the patient, such that the network increases the drive current through the patient as a frequency of the drive current increases. The measurement circuitry may comprise a variable gain that decreases when the frequency is increases and the drive current increases.

BRIEF DESCRIPTION OF THE DRAWINGS

FIG. 1D shows a printed circuit boards and electronic components over the adherent patch, as in FIG. 1C;

FIG. 1D shows an equivalent circuit that can be used to determine optimal frequencies for determining patient hydration, according to embodiments of the present invention;

DETAILED DESCRIPTION OF THE INVENTION

Embodiments of the present invention relate to patient monitoring. Although embodiments make specific reference to monitoring impedance and electrocardiogram signals with an adherent patch, the system methods and device described herein may be applicable to many application in which physiological monitoring is used, for example physiological monitoring with implantable devices.

In many embodiments, the adherent devices described herein may be used for 90 day monitoring, or more, and may comprise completely disposable components and/or reusable components, and can provide reliable data acquisition and transfer. In many embodiments, the patch is configured for patient comfort, such that the patch can be worn and/or tolerated by the patient for extended periods, for example 90 days or more. In many embodiments, the adherent patch comprises a tape, which comprises a material, preferably breathable, with an adhesive, such that trauma to the patient skin can be minimized while the patch is worn for the extended period. In many embodiments, the printed circuit board comprises a flex printed circuit board that can flex with the patient to provide improved patient comfort.

Figure 1A:
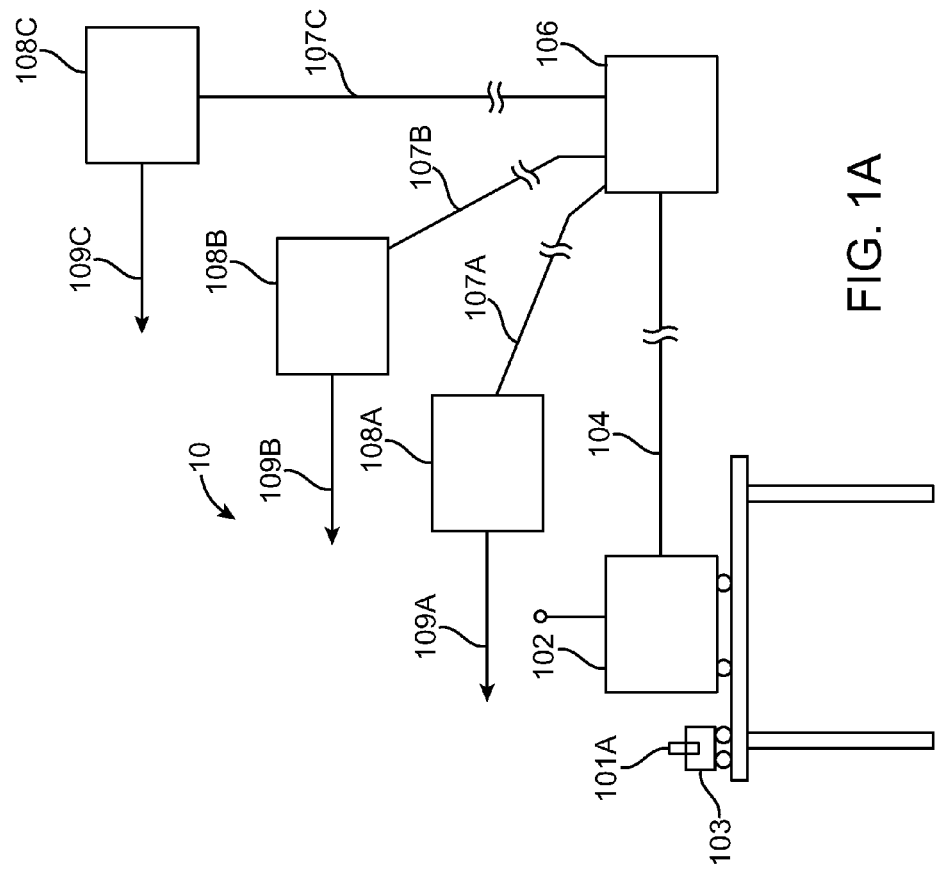
FIG. 1A shows a patient and a monitoring system comprising an adherent device, according to embodiments of the present invention.
Figure 1A:
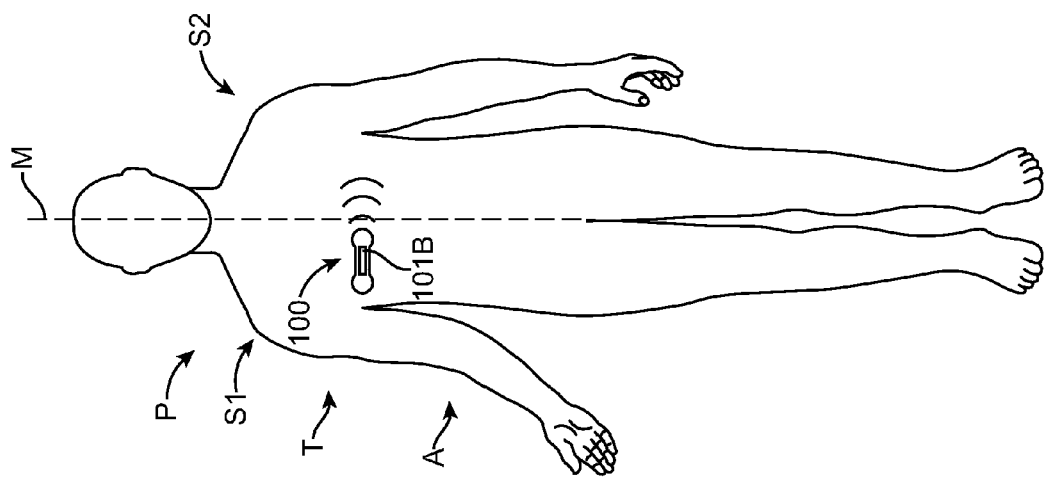

FIG. 1A shows a patient P and a monitoring system 10. Patient P comprises a midline M, a first side S1, for example a right side, and a second side S2, for example a left side. Monitoring system 10 comprises an adherent device 100. Adherent device 100 can be adhered to a patient P at many locations, for example thorax T of patient P. In many embodiments, the adherent device may adhere to one side of the patient, from which side data can be collected. Work in relation with embodiments of the present invention suggests that location on a side of the patient can provide comfort for the patient while the device is adhered to the patient.

Monitoring system 10 includes components to transmit data to a remote center 106. Adherent device 100 can communicate wirelessly to an intermediate device 102, for example with a single wireless hop from the adherent device on the patient to the intermediate device. Intermediate device 102 can communicate with remote center 106 in many ways, for example with an internet connection. In many embodiments, monitoring system 10 comprises a distributed processing system with at least one processor on device 100, at least one processor on intermediate device 102, and at least one process at remote center 106, each of which processors is in electronic communication with the other processors. Remote center 106 can be in communication with a health care provider 108A with a communication system 107A, such as the Internet, an intranet, phone lines, wireless and/or satellite phone. Health care provider 108A, for example a family member, can be in communication with patient P with a communication, for example with a two way communication system, as indicated by arrow 109A, for example by cell phone, email, landline. Remote center 106 can be in communication with a health care professional, for example a physician 108B, with a communication system 107B, such as the Internet, an intranet, phone lines, wireless and/or satellite phone. Physician 108B can be in communication with patient P with a communication, for example with a two way communication system, as indicated by arrow 109B, for example by cell phone, email, landline. Remote center 106 can be in communication with an emergency responder 108C, for example a 911 operator and/or paramedic, with a communication system 107C, such as the Internet, an intranet, phone lines, wireless and/or satellite phone. Emergency responder 108C can travel to the patient as indicated by arrow 109C. Thus, in many embodiments, monitoring system 10 comprises a closed loop system in which patient care can be monitored and implemented from the remote center in response to signals from the adherent device.

In many embodiments, the adherent device may continuously monitor physiological parameters, communicate wirelessly with a remote center, and provide alerts when necessary. The system may comprise an adherent patch, which attaches to the patient's thorax and contains sensing electrodes, battery, memory, logic, and wireless communication capabilities. In some embodiments, the patch can communicates with the remote center, via the intermediate device in the patient's home. In the many embodiments, the remote center receives the data and applies the prediction algorithm. When a flag is raised, the center may communicate with the patient, hospital, nurse, and/or physician to allow for therapeutic intervention to prevent decompensation.

The adherent device may be affixed and/or adhered to the body in many ways. For example, with at least one of the following an adhesive tape, a constant-force spring, suspenders around shoulders, a screw-in microneedle electrode, a pre-shaped electronics module to shape fabric to a thorax, a pinch onto roll of skin, or transcutaneous anchoring. Patch and/or device replacement may occur with a keyed patch (e.g. two-part patch), an outline or anatomical mark, a low-adhesive guide (place guide|remove old patch|place new patch|remove guide), or a keyed attachment for chatter reduction. The patch and/or device may comprise an adhesiveless embodiment (e.g. chest strap), and/or a low-irritation adhesive model for sensitive skin. The adherent patch and/or device can comprise many shapes, for example at least one of a dogbone, an hourglass, an oblong, a circular or an oval shape.

In many embodiments, the adherent device may comprise a reusable electronics module with replaceable patches (the module collects cumulative data for approximately 90 days) and/or the entire adherent component (electronics+ patch) may be disposable. In a completely disposable embodiment, a "baton" mechanism may be used for data transfer and retention, for example baton transfer may include baseline information. In some embodiments, the device may have a rechargeable module, and may use dual battery and/or electronics modules, wherein one module 101A can be recharged using a charging station 103 while the other module 101B is placed on the adherent device. In some embodiments, the intermediate device 102 may comprise the charging module, data transfer, storage and/or transmission, such that one of the electronics modules can be placed in the intermediate device for charging and/or data transfer while the other electronics module is worn by the patient.

In many embodiments, the system can perform the following functions: initiation, programming, measuring, storing, analyzing, communicating, predicting, and displaying. The adherent device may contain a subset of the following physiological sensors: bioimpedance, respiration, respiration rate variability, heart rate (ave, min, max), heart rhythm, HRV, HRT, heart sounds (e.g. S3), respiratory sounds, blood pressure, activity, posture, wake/sleep, orthopnea, temperature/ heat flux, and weight. The activity sensor may be one of the following: ball switch, accelerometer, minute ventilation, HR, bioimpedance noise, skin temperature/heat flux, BP, muscle noise, posture.

In many embodiments, the patch wirelessly communicates with a remote center. In some embodiments, the communication may occur directly (via a cellular or Wi-Fi network), or indirectly through intermediate device 102. Intermediate device 102 may consist of multiple devices which communicate wired or wirelessly to relay data to remote center 106.

In many embodiments, instructions are transmitted from a remote site to a processor supported with the patient, and the processor supported with the patient can receive updated instructions for the patient treatment and/or monitoring, for example while worn by the patient.

Figure 1B:
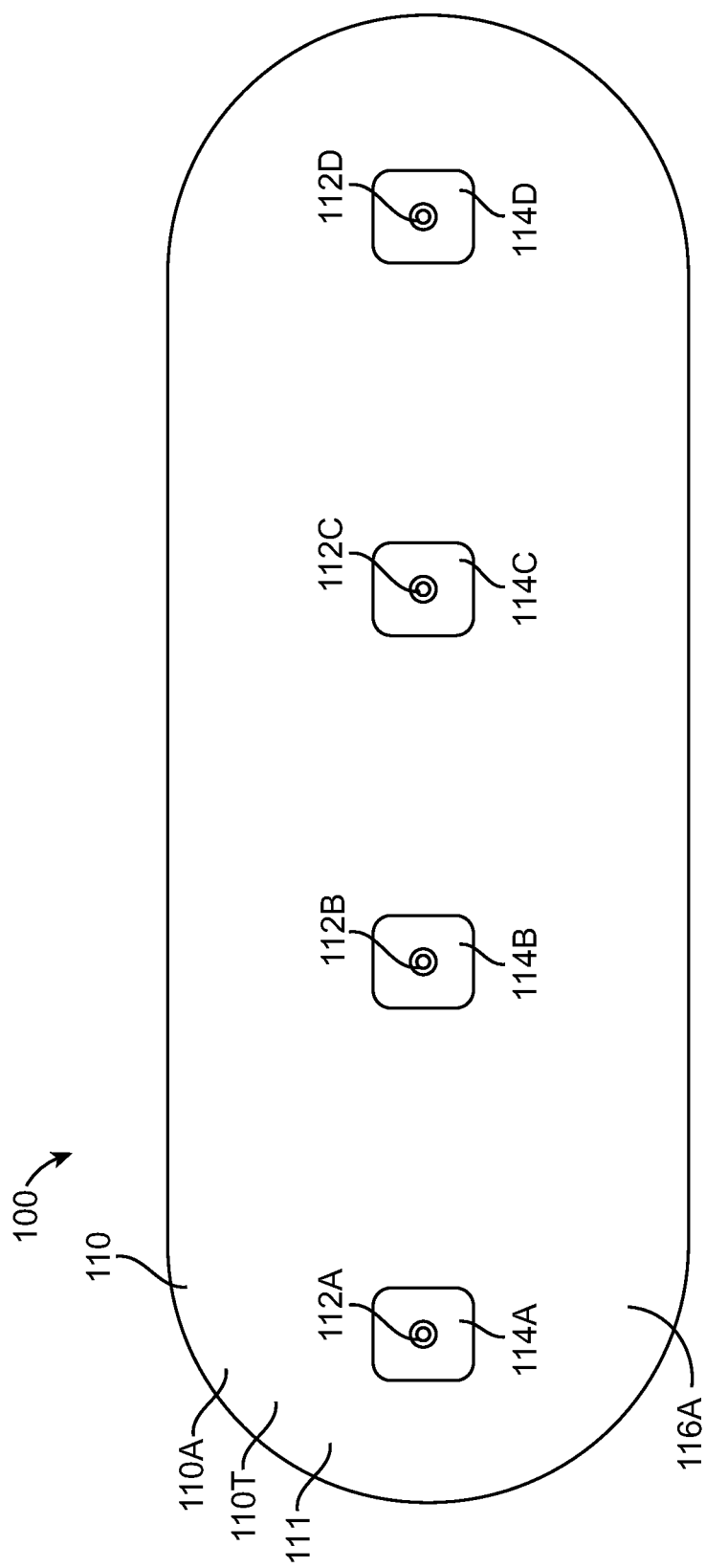
FIG. 1B shows a bottom view of the adherent device as in FIG. 1A comprising an adherent patch.

FIG. 1B shows a bottom view of adherent device 100 as in FIG. 1A comprising an adherent patch 110. Adherent patch 110 comprises a first side, or a lower side 110A, that is oriented toward the skin of the patient when placed on the patient. In many embodiments, adherent patch 110 comprises a tape 110T which is a material, preferably breathable, with an adhesive 116A. Patient side 110A comprises adhesive 116A to adhere the patch 110 and adherent device 100 to patient P. Electrodes 112A, 112B, 112C and 112D are affixed to adherent patch 110. In many embodiments, at least four electrodes are attached to the patch, for example six electrodes. In some embodiments the patch comprises two electrodes, for example two electrodes to measure the electrocardiogram (ECG) of the patient. Gel 114A, gel 114B, gel 114C and gel 114D can each be positioned over electrodes 112A, 112B, 112C and 112D, respectively, to provide electrical conductivity between the electrodes and the skin of the patient. In many embodiments, the electrodes can be affixed to the patch 110, for example with known methods and structures such as rivets, adhesive, stitches, etc. In many embodiments, patch 110 comprises a breathable material to permit air and/or vapor to flow to and from the surface of the skin.

Figure 1C:
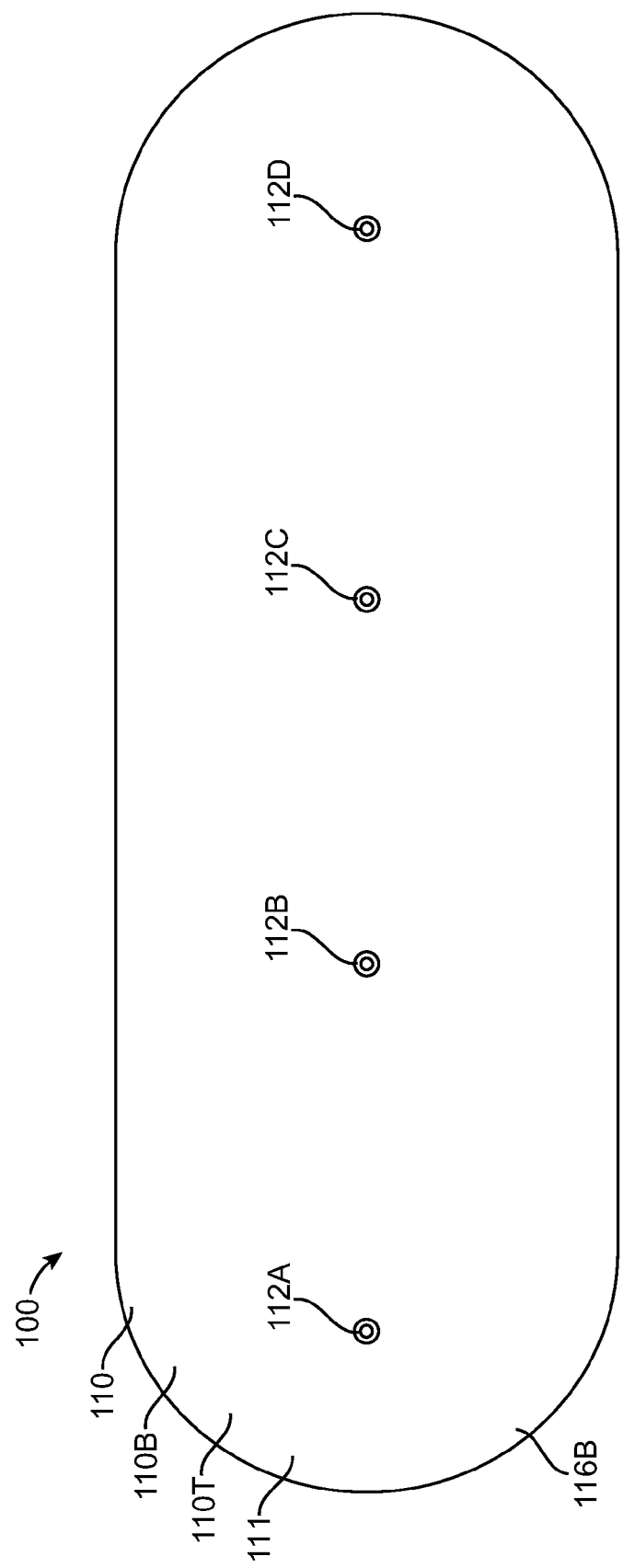
FIG. 1C shows a top view of the adherent patch, as in FIG. 1B.

FIG. 1C shows a top view of the adherent patch 100, as in FIG. 1B. Adherent patch 100 comprises a second side, or upper side 110B. In many embodiments, electrodes 110A, 110B, 110C and 110D extend from lower side 110A through the adherent patch to upper side 110B. In some embodiments, an adhesive 116B can be applied to upper side 110B to adhere structures, for example electronic structures, to the patch such that the patch can support the electronics and other structures when the patch is adhered to the patient. The PCB comprise completely flex PCB, rigid PCB combined flex PCB and/or rigid PCB boards connected by cable.

FIG. 1D shows a printed circuit boards and electronic components over adherent patch 110, as in FIG. 1C. In some embodiments, a printed circuit board (PCB), for example flex PCB 120, may be connected to upper side 100B of patch 110 with connectors 122A, 122B, 122C and 122D. Flex PCB 120 can include traces 123A, 123B, 123C and 123D that extend to connectors 122A, 122B, 122C and 122D, respectively, on the flex PCB. Connectors 122A, 122B, 122C and 122D can be positioned on flex PCB 120 in alignment with electrodes 112A, 112B, 112C and 112D so as to electrically couple the flex PCB with the electrodes. In some embodiments, connectors 122A, 122B, 122C and 122D may comprise insulated wires that provide strain relief between the PCB and the electrodes. In some embodiments, additional PCB's, for example rigid PCB's 120A, 120B, 120C and 120D, can be connected to flex PCB 120. Electronic components 130 can be connected to flex PCB 120 and/or mounted thereon. In some embodiments, electronic components 130 can be mounted on the additional PCB's.

Electronic components 130 comprise components to take physiologic measurements, transmit data to remote center 106 and receive commands from remote center 106. In many embodiments, electronics components 130 may comprise known low power circuitry, for example complementary metal oxide semiconductor (CMOS) circuitry components. Electronics components 130 comprise an activity sensor and activity circuitry 134, impedance circuitry 136 and electrocardiogram circuitry, for example ECG circuitry 136. In some embodiments, electronics circuitry 130 may comprise a microphone and microphone circuitry 142 to detect an audio signal from within the patient, and the audio signal may comprise a heart sound and/or a respiratory sound, for example an S3 heart sound and a respiratory sound with rales and/or crackles. Electronics circuitry 130 may comprise a temperature sensor, for example a thermistor, and temperature sensor circuitry 144 to measure a temperature of the patient, for example a temperature of a skin of the patient.

Work in relation to embodiments of the present invention suggests that skin temperature may effect impedance and/or hydration measurements, and that skin temperature measurements may be used to correct impedance and/or hydration measurements. In some embodiments, increase in skin temperature or heat flux can be associated with increased vasodilation near the skin surface, such that measured impedance measurement decreased, even through the hydration of the patient in deeper tissues under the skin remains substantially unchanged. Thus, use of the temperature sensor can allow for correction of the hydration signals to more accurately assess the hydration, for example extra cellular hydration, of deeper tissues of the patient, for example deeper tissues in the thorax.

Electronics circuitry 130 may comprise a processor 146. Processor 146 comprises a tangible medium, for example read only memory (ROM), electrically erasable programmable read only memory (EEPROM) and/or random access memory (RAM). Electronic circuitry 130 may comprise real time clock and frequency generator circuitry 148. In some embodiments, processor 136 may comprise the frequency generator and real time clock. The processor can be configured to control a collection and transmission of data from the impedance circuitry electrocardiogram circuitry and the accelerometer. In many embodiments, device 100 comprise a distributed processor system, for example with multiple processors on device 100.

In many embodiments, electronics components 130 comprise wireless communications circuitry 132 to communicate with remote center 106. The wireless communication circuitry can be coupled to the impedance circuitry, the electrocardiogram circuitry and the accelerometer to transmit to a remote center with a communication protocol at least one of the hydration signal, the electrocardiogram signal or the inclination signal. In specific embodiments, wireless communication circuitry is configured to transmit the hydration signal, the electrocardiogram signal and the inclination signal to the remote center with a single wireless hop, for example from wireless communication circuitry 132 to intermediate device 102. The communication protocol comprises at least one of Bluetooth, Zigbee, WiFi, WiMax, IR, amplitude modulation or frequency modulation. In many embodiments, the communications protocol comprises a two way protocol such that the remote center is capable of issuing commands to control data collection.

In some embodiments, intermediate device 102 comprises a data collection system to collect and store data from the wireless transmitter. The data collection system can be configured to communicate periodically with the remote center. In many embodiments, the data collection system can transmit data in response to commands from remote center 106 and/or in response to commands from the adherent device.

Activity sensor and activity circuitry 134 can comprise many known activity sensors and circuitry. In many embodiments, the accelerometer comprises at least one of a piezoelectric accelerometer, capacitive accelerometer or electromechanical accelerometer. The accelerometer may comprises a 3-axis accelerometer to measure at least one of an inclination, a position, an orientation or acceleration of the patient in three dimensions. Work in relation to embodiments of the present invention suggests that three dimensional orientation of the patient and associated positions, for example sitting, standing, lying down, can be very useful when combined with data from other sensors, for example ECG data and/or hydration data.

Impedance circuitry 136 can generate both hydration data and respiration data. In many embodiments, impedance circuitry 136 is electrically connected to electrodes 112A, 112B, 112C and 112D such that electrodes 112A and 112D comprise outer electrodes that are driven with a current, or force electrodes. The current delivered between electrodes 112A and 112D generates a measurable voltage between electrodes 112B and 112C, such that electrodes 112B and 112C comprise inner electrodes, or measurement electrodes that measure the voltage in response to the current from the force electrodes. The voltage measured by the measurement electrodes can be used to determine the hydration of the patient.

FIG. 1D1 shows an equivalent circuit 152 that can be used to determine optimal frequencies for measuring patient hydration. Work in relation to embodiments of the present invention indicates that the frequency of the current and/or voltage at the force electrodes can be selected so as to provide impedance signals related to the extracellular and/or intracellular hydration of the patient tissue. Equivalent circuit 152 comprises an intracellular resistance 156, or R(ICW) in series with a capacitor 154, and an extracellular resistance 158, or R(ECW). Extracellular resistance 158 is in parallel with intracellular resistance 156 and capacitor 154 related to capacitance of cell membranes. In many embodiments, impedances can be measured and provide useful information over a wide range of frequencies, for example from about 0.5 kHz to about 200 KHz. Work in relation to embodiments of the present invention suggests that extracellular resistance 158 can be significantly related extracellular fluid and to cardiac decompensation, and that extracellular resistance 158 and extracellular fluid can be effectively measured with frequencies in a range from about 0.5 kHz to about 20 kHz, for example from about 1 kHz to about 10 kHz. In some embodiments, a single frequency can be used to determine the extracellular resistance and/or fluid. As sample frequencies increase from about 10 kHz to about 20 kHz, capacitance related to cell membranes decrease the impedance, such that the intracellular fluid contributes to the impedance and/or hydration measurements. Thus, many embodiments of the present invention employ measure hydration with frequencies from about 0.5 kHz to about 20 kHz to determine patient hydration.

In many embodiments, impedance circuitry 136 can be configured to determine respiration of the patient. In specific embodiments, the impedance circuitry can measure the hydration at 25 Hz intervals, for example at 25 Hz intervals using impedance measurements with a frequency from about 0.5 kHz to about 20 kHz.

ECG circuitry 138 can generate electrocardiogram signals and data from electrodes 112A, 112B, 112C and 112D. In some embodiments, ECG circuitry 138 is connected to inner electrodes 112B and 122C, which may comprise measurement electrodes of the impedance circuitry as described above. In some embodiments, the inner electrodes may be positioned near the outer electrodes to increase the voltage of the ECG signal measured by ECG circuitry 138. In some embodiments, the ECG circuitry can share components with the impedance circuitry.

Figure 1E:
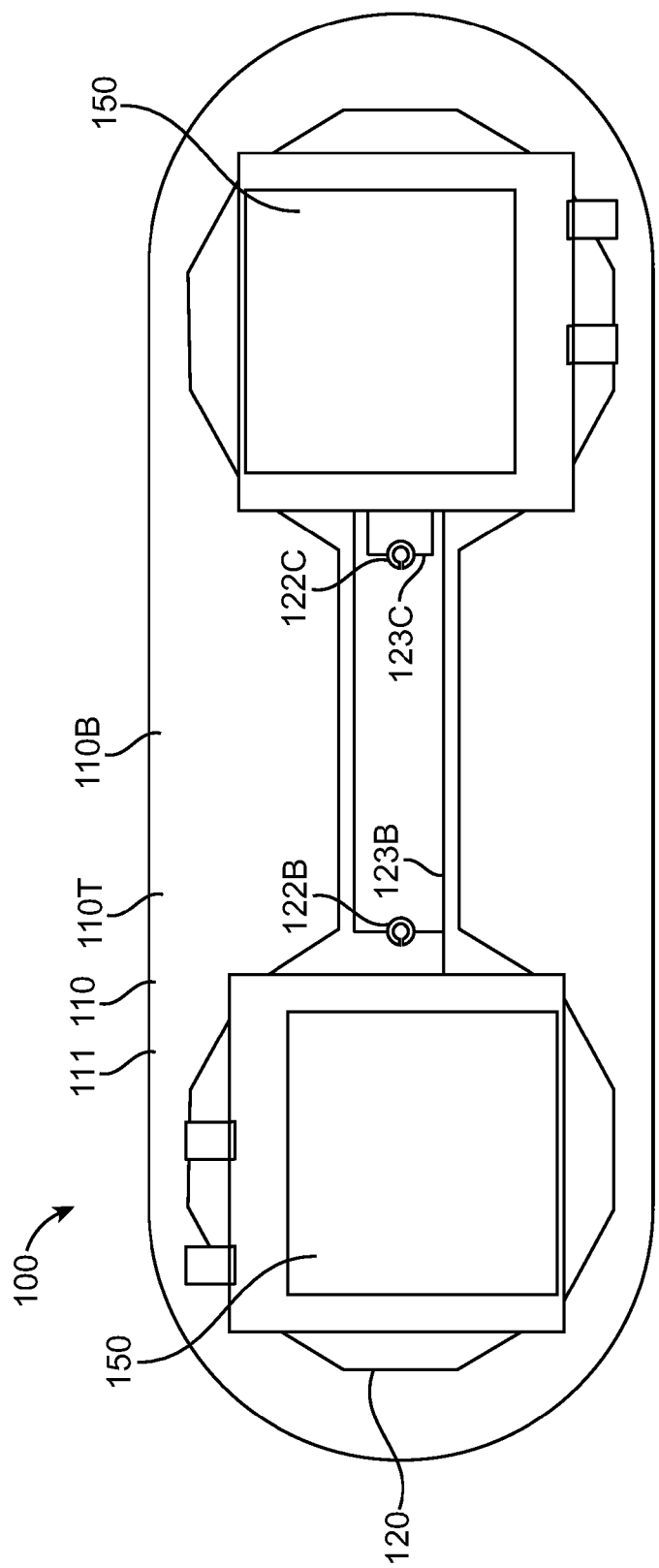
FIG. 1E shows batteries positioned over the printed circuit board and electronic components as in FIG. 1D.

FIG. 1E shows batteries 150 positioned over the flex printed circuit board and electronic components as in FIG. 1D. Batteries 150 may comprise rechargeable batteries that can be removed and/or recharged. In some embodiments, batteries 150 can be removed from the adherent patch and recharged and/or replaced.

Figure 1F:
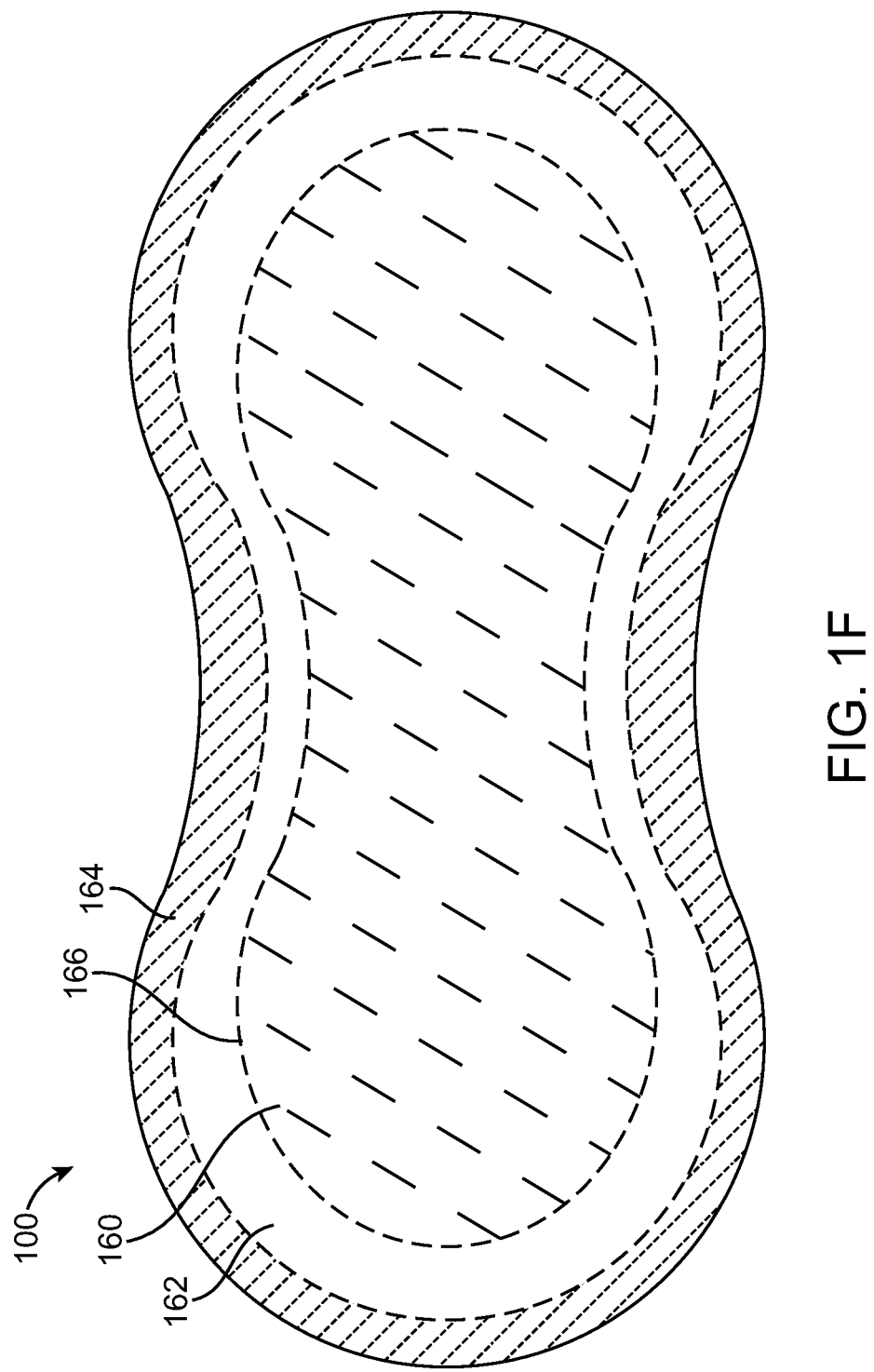
FIG. 1F shows a top view of an electronics housing and a breathable cover over the batteries, electronic components and printed circuit board as in FIG. 1E.

FIG. 1F shows a top view of a cover 162 over the batteries, electronic components and flex printed circuit board as in FIG. 1E. In many embodiments, an electronics housing 160 may be disposed under cover 162 to protect the electronic components, and in some embodiments electronics housing 160 may comprise an encapsulant over the electronic components and PCB. In some embodiments, cover 162 can be adhered to adhesive patch with an adhesive 164 on an underside of cover 162. In some embodiments, electronics housing 160 can be adhered to cover 162 with an adhesive 166 where cover 162 contacts electronics housing 160. In many embodiments, electronics housing 160 may comprise a water proof material, for example a sealant adhesive such as epoxy or silicone coated over the electronics components and/or PCB. In some embodiments, electronics housing 160 may comprise metal and/or plastic. Metal or plastic may be potted with a material such as epoxy or silicone.

Cover 162 may comprise many known biocompatible cover, casing and/or housing materials, such as elastomers, for example silicone. The elastomer may be fenestrated to improve breathability. In some embodiments, cover 162 may comprise many known breathable materials, for example polyester, polyamide, and/or elastane (Spandex). The breathable fabric may be coated to make it water resistant, waterproof, and/or to aid in wicking moisture away from the patch.

Figure 1G:
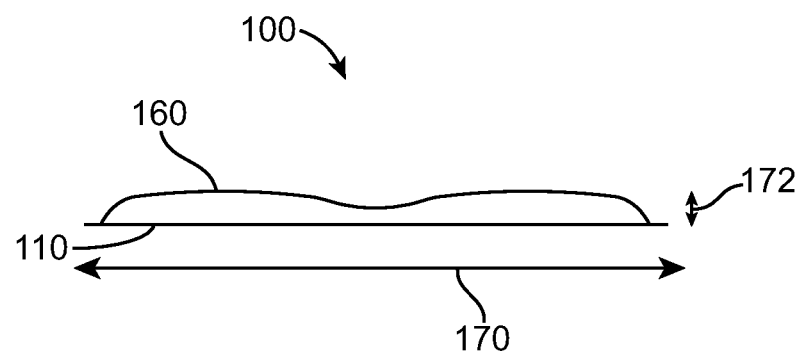
FIG. 1G shows a side view of the adherent device as in FIGS. 1A to 1F.

FIG. 1G shows a side view of adherent device 100 as in FIGS. 1A to 1F. Adherent device 100 comprises a maximum dimension, for example a length 170 from about 4 to 10 inches (from about 100 mm to about 250 mm), for example from about 6 to 8 inches (from about 150 mm to about 200 mm). In some embodiments, length 170 may be no more than about 6 inches (no more than about 150 mm). Adherent device 100 comprises a thickness 172. Thickness 172 may comprise a maximum thickness along a profile of the device. Thickness 172 can be from about 0.2 inches to about 0.4 inches (from about 5 mm to about 10 mm), for example about 0.3 inches (about 7.5 mm).

Figure 1H:
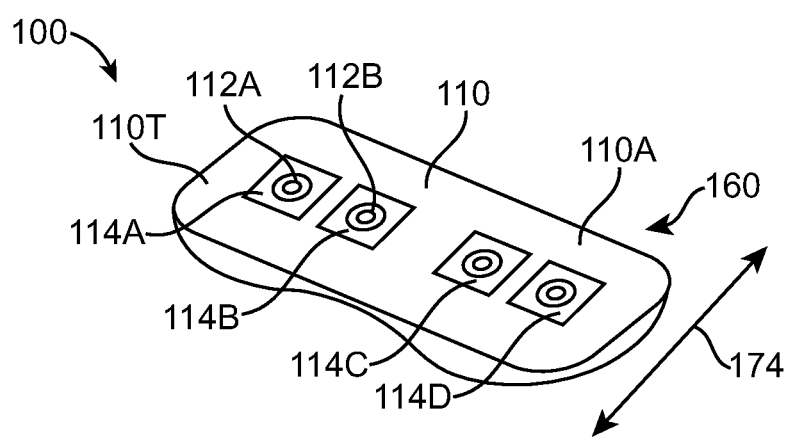
FIG. 1H shown a bottom isometric view of the adherent device as in FIGS. 1A to 1G.

FIG. 1H shown a bottom isometric view of adherent device 100 as in FIGS. 1A to 1G. Adherent device 100 comprises a width 174, for example a maximum width along a width profile of adherent device 100. Width 174 can be from about 2 to about 4 inches (from about 50 mm to 100 mm), for example about 3 inches (about 75 mm).

Figure 1K:
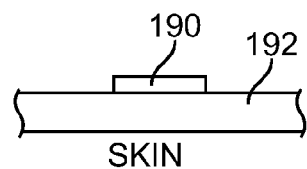
FIG. 1K shows at least one electrode configured to electrically couple to a skin of the patient through a breathable tape, according to embodiments of the present invention.
Figure 1I:
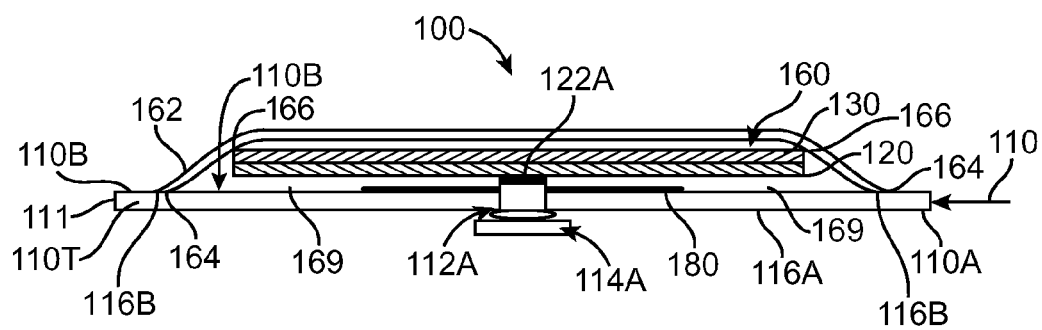
FIGS. 1I and 1J show a side cross-sectional view and an exploded view, respectively, of the adherent device as in FIGS. 1A to 1H.
Figure 1J:
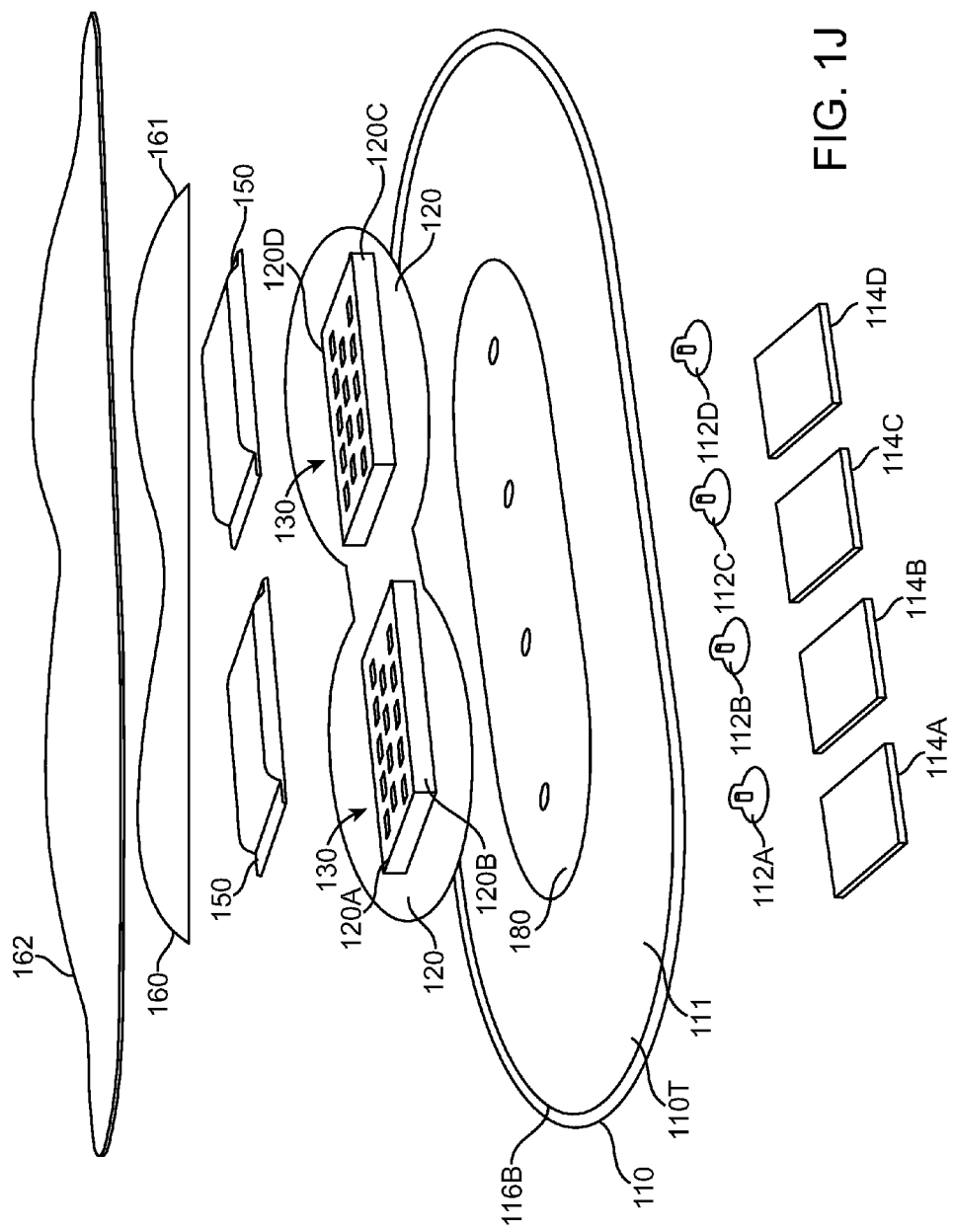

FIGS. 1I and 1J show a side cross-sectional view and an exploded view, respectively, of adherent device 100 as in FIGS. 1A to 1H. Device 100 comprises several layers. Gel 114A, or gel layer, is positioned on electrode 112A to provide electrical conductivity between the electrode and the skin. Electrode 112A may comprise an electrode layer. Adhesive patch 110 may comprise a layer of breathable tape 110T, for example a known breathable tape, such as tricot-knit polyester fabric. An adhesive 116A, for example a layer of acrylate pressure sensitive adhesive, can be disposed on underside 110A of patch 110. A gel cover 180, or gel cover layer, for example a polyurethane non-woven tape, can be positioned over patch 110 comprising the breathable tape. A PCB layer, for example flex PCB 120, or flex PCB layer, can be positioned over gel cover 180 with electronic components 130 connected and/or mounted to flex PCB 120, for example mounted on flex PCB so as to comprise an electronics layer disposed on the flex PCB. In many embodiments, the adherent device may comprise a segmented inner component, for example the PCB, for limited flexibility. In many embodiments, the electronics layer may be encapsulated in electronics housing 160 which may comprise a waterproof material, for example silicone or epoxy. In many embodiments, the electrodes are connected to the PCB with a flex connection, for example trace 123A of flex PCB 120, so as to provide strain relive between the electrodes 112A, 112B, 112C and 112D and the PCB. Gel cover 180 can inhibit flow of gel 114A and liquid. In many embodiments, gel cover 180 can inhibit gel 114A from seeping through breathable tape 110T to maintain gel integrity over time. Gel cover 180 can also keep external moisture from penetrating into gel 114A. In many embodiments, cover 162 can encase the flex PCB and/or electronics and can be adhered to at least one of the electronics, the flex PCB or the adherent patch, so as to protect the device. In some embodiments, cover 162 attaches to adhesive patch 110 with adhesive 116B, and cover 162 is adhered to the PCB module with an adhesive 161 on the upper surface of the electronics housing. Cover 162 can comprise many known biocompatible cover, housing and/or casing materials, for example silicone. In many embodiments, cover 162 comprises an outer polymer cover to provide smooth contour without limiting flexibility. In some embodiments, cover 162 may comprise a breathable fabric. Cover 162 may comprise many known breathable fabrics, for example breathable fabrics as described above. In some embodiments, the breathable fabric may comprise polyester, polyamide, and/or elastane (Spandex) to allow the breathable fabric to stretch with body movement. In some embodiments, the breathable tape may contain and elute a pharmaceutical agent, such as an antibiotic, anti-inflammatory or antifungal agent, when the adherent device is placed on the patient.

In many embodiments, the breathable tape of adhesive patch 110 comprises a first mesh with a first porosity and gel cover 180 comprises a breathable tape with a second mesh porosity, in which the second porosity is less than the first porosity to inhibit flow of the gel through the breathable tape.

In many embodiments, a gap 169 extends from adherent patch 110 to the electronics module and/or PCB, such that breathable tape 110T can breath to provide patient comfort.

In many embodiments, the adherent device comprises a patch component and at least one electronics module. The patch component may comprise adhesive patch 110 comprising the breathable tape with adhesive coating 116A, at least one electrode 114A and gel 114, for example a gel coating. The at least one electronics module can be is separable from the patch component. In many embodiments, the at least one electronics module comprises the flex printed circuit board 120, electronic component 130, electronics housing 160 and waterproof cover 162, such that the flex printed circuit board, electronic components electronics housing and water proof cover are reusable and/or removable for recharging and data transfer, for example as described above. In many embodiments, adhesive 116B is coated on upper side 110A of adhesive patch 110B, such that the electronics module, or electronics layers, can be adhered to and/or separated from the adhesive component, or adhesive layers. In specific embodiments, the electronic module can be adhered to the patch component with a releasable connection, for example with Velcro™, a known hook and loop connection, and/or snap directly to the electrodes. In some embodiments, two electronics modules can be provided, such that one electronics module can be worn by the patient while the other is charged as described above.

In many embodiments, at least one electrode 112A extends through at least one aperture in the breathable tape 110.

In some embodiments, the adhesive patch may comprise a medicated patch that releases a medicament, such as antibiotic, beta-blocker, ACE inhibitor, diuretic, or steroid to reduce skin irritation. In some embodiments, the adhesive patch may comprise a thin, flexible, breathable patch with a polymer grid for stiffening. This grid may be anisotropic, may use electronic components to act as a stiffener, may use electronics-enhanced adhesive elution, and may use an alternating elution of adhesive and steroid.

FIG. 1K shows at least one electrode 190 configured to electrically couple to a skin of the patient through a breathable tape 192. In many embodiments, at least one electrode 190 and breathable tape 192 comprise electrodes and materials similar to those described above. Electrode 190 and breathable tape 192 can be incorporated into adherent devices as described above, so as to provide electrical coupling between the skin an electrode through the breathable tape, for example with the gel.

Figure 2A:
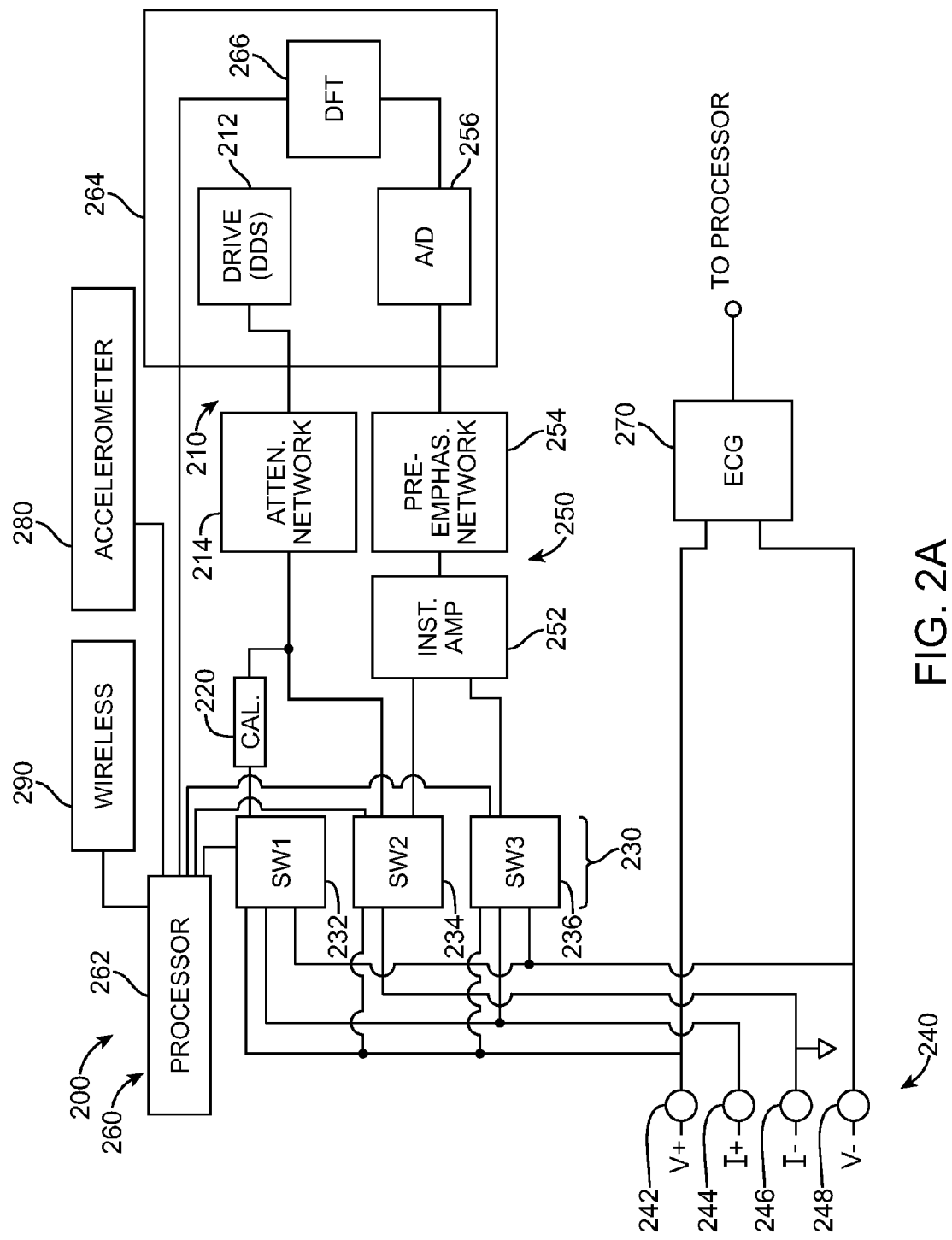
FIG. 2A shows a simplified schematic illustration of a circuit diagram for measuring patient impedance, according to embodiments of the present invention.

FIG. 2A shows a simplified schematic illustration of circuitry 200 for measuring patient signals, such as impedance signals to measure hydration, ECG signals. Circuitry 200 comprises drive circuitry 210 to drive a current through the patient tissue, and measurement circuitry 250 to measure an impedance signal from the patient tissue. Circuitry 200 may comprise at least four electrodes 240 to couple drive circuitry 210 and measurement circuitry 250 to the patient tissue. Circuitry 200 comprises calibration circuitry 220 to calibrate the drive circuitry and measurement circuitry. Circuitry 200 may comprise a processor system 260 that comprises at least one processor, for example a processor 262 on the adherent device as described above. Circuitry 200 may comprise at least one switch 230 that can be used to select for measurement either on board calibration circuitry 220 or electrodes 240 that are coupled to the skin of the patient. Circuitry 200 may comprise ECG circuitry 270 to measure electrocardiogram signals from the patient, accelerometer 280 to measure patient position and/or activity, and wireless circuitry 290 to transmit the data.

Drive circuitry 210 may comprise a drive module 212. Drive module 212 can be used to generate a drive current at a selected frequency. For example, drive module 212 may comprise direct digital synthesis (DDS) and digital to analog conversion (DAC) and amplifiers to generate the drive current at the selected frequency. The amplifiers to generate the drive current may comprise a gain, and in some embodiments the gain of the drive current amplifiers increases with increasing frequency. In some embodiments, drive module 212 may comprise analog electronics, for example a frequency generator to generate the drive current at the selected frequency. The drive current may comprise an AC component at the selected frequency and a DC component. Drive circuitry 210 comprises circuitry to adjust the current delivered to the patient in response to the selected frequency. In many embodiments, drive circuitry 210 can increase the current delivered to the patient as the drive frequency increases, such that the amount of current complies with safe current requirements, for example known AAMI ES1 requirements. The drive current is generally below a safety threshold that corresponds to 10 µA for frequencies below 1 kHz, increases by 10 µA per decade kHz from 1 kHz to 100 kHz, and remains at 1 mA for frequencies above 100 kHz, for example from 100 kHz to 1 MHz. In many embodiments, drive circuitry 210 comprises an attenuation network that decreases current from the drive module to the tissue. In many embodiments, the attenuation of drive current from the drive module decreases with increasing frequency, such that the amount of current delivered to the patient increases with increasing frequency. In specific embodiments, attenuation circuitry 212 may comprise a high pass RC circuit network such that the current delivered to tissue increases from about 200 Hz to about 1 kHz, for example with a corner frequency, $f_c$, within a range from about 200 Hz to about 1 kHz. Alternatively or in combination, drive circuitry 210 may comprise a high pass amplifier that increases the gain of current delivered to the patient as the selected frequency increases.

Calibration circuitry 220 can comprise components of known impedance to calibrate circuitry 200. Calibration circuitry 220 can be connected to drive circuitry 210 and measurement circuitry 250 to calibrate the electronics of circuitry 200, for example drive circuitry 210 and measurement circuitry 250. In specific embodiments, calibration circuitry 220 comprises a resistor of known resistance that can be used to calibrate drive circuitry 210 and measurement circuitry 250. Calibration circuitry 220 may comprise a substantial resistance with very little reactance, for example resistance may comprise at least 90% of the magnitude of the impedance of calibration circuitry 220. The use of calibration circuitry that comprises substantial resistance can facilitate calibration, as phase delay and amplitude changes in the measured calibration signal may be attributed to changes in drive circuitry 210 and measurement circuitry 250. In many embodiments, the resistor of calibration circuitry 220 comprises a known resistance that is close to the impedance of tissue measured such that the calibration circuitry comprises an impedance with a magnitude within the range of physiologic tissue impedances likely to be measured with the electrodes, for example from about 10 Ohms to about 200 Ohms. In some embodiments, calibration circuitry 220 may comprises a plurality of selectable resistors to select a resistance that is close to the measured tissue impedance.

At least one electrode 240 comprises at least two drive electrodes, for example V+ electrode 244 and V− electrode 248. The at least two drive electrodes can be coupled to drive circuitry 210 to pass a current through the tissue of the patient. At least one electrode 240 comprises at least two measurement electrodes, for example I+ electrode 244 and I− electrode 246. The at least two measurement electrodes can be coupled to measurement circuitry 250 to measure an impedance signal from the tissue, for example a voltage drop across the tissue from the current passed through the tissue.

Circuitry 200 may comprise at least one switch 230. At least one switch 230 may comprise a first package of high performance switches SW1, a second package of high performance switches SW2 and a third package of high performance switches SW3. At least one switch 230 can be configured in many ways. In specific embodiments, a first configuration of at least one switch 230 couples drive circuitry 210 and measurement circuitry 250 to calibration circuitry 230 to measure an impedance signal from calibration circuitry 230 to calibrate the circuitry. A second configuration of at least one switch 230 couples drive circuitry 210 to the at least two drive electrodes and measurement circuitry 250 to the at least two measurement electrodes to measure the impedance of the tissue of the patient.

Although at least one switch 230 is shown, in some embodiments calibration can be performed without switches, for example with substantially parallel drive and measurement circuits. In specific embodiments, drive circuitry 210 may comprise substantially similar parallel drive circuits with one of the parallel drive circuits coupled to the resistance circuitry and the other of the parallel drive circuits coupled to the tissue with the drive electrodes. Measurement circuitry 250 may comprise substantially similar measurement circuits with one of the substantially similar measurement circuits coupled to the resistance circuitry and the other of the substantially similar measurement circuits coupled to the tissue with the measurement electrodes. Thus, in at least some embodiments, calibration based on the resistance circuitry can be performed without the at least one switch.

Measurement circuitry 250 may comprise a differential amplifier, for example an instrumentation amplifier 252 with high input impedance. Instrumentation amplifier 252 may comprise known instrumentation amplifier circuits. Measurement circuitry can be configured with a variable gain that decreases as the current to the tissue increases. Measurement circuitry 250 may comprise a pre-emphasis before analog to digital converter 256, for example de-emphasis network that decreases the gain of the measurement circuitry as the frequency increases. In specific embodiments, an RC network can be used to provide a decrease in gain of the measurement circuitry with an increase in drive frequency and drive current. Measurement circuitry 250 may comprise an analog to digital converter 256 (A/D) to convert the analog measurement signal to a digital measurement signal the analog to digital converter communicates the digitized measurement signal to the processor system.

Circuitry 200 may comprise ECG circuitry 270. ECG circuitry 270 can be connected to the drive electrodes of at least one electrode 240 and may be connected to the measurement electrodes of at least one electrode 240 to measure the ECG signal from the patient. ECG circuitry may comprise known ECG circuitry with variable gain, for example known instrumentation amplifiers and known bandpass filters to select the frequencies of the ECG signal with variable gain. ECG circuitry 270 can be connected to processor 262 to process the ECG signals.

Circuitry 200 may comprise an accelerometer 280 to measure patient orientation, acceleration and/or activity of the patient. Accelerometer 280 may comprise many known accelerometers. Accelerometer 280 may be connected to processor 262 to process signals from accelerometer 280.

Circuitry 200 may comprise wireless circuitry 290. Wireless circuitry 290 may comprise known wireless circuitry for wireless communication from the device. Wireless communications circuitry 290 can communicate with remote center as described above. The wireless communication circuitry can be coupled to the impedance circuitry, the electrocardiogram circuitry and the accelerometer to transmit to a remote center with a communication protocol at least one of the hydration signal, the electrocardiogram signal or the inclination signal from the accelerometer. In specific embodiments, wireless communication circuitry is configured to transmit the hydration signal, the electrocardiogram signal and the inclination signal to the remote center with a single wireless hop, for example from wireless communication circuitry 290 to the intermediate device as described above. The communication protocol may comprise at least one of Bluetooth, Zigbee, WiFi, WiMax, IR, amplitude modulation or frequency modulation. In many embodiments, the communications protocol comprises a two way protocol such that the remote center is capable of issuing commands to control data collection.

Processor system 260 may comprise processors in addition to processor 262, for example a remote processor as described above. Processor 262 comprises a tangible medium that can be configured with instructions, for example known processor memory. Processor 262 may comprise a known single chip processor with random access memory (RAM), read only memory (ROM), erasable read only memory (EPROM) and a central processing unit. Processor system 260 may also comprise an onboard impedance converter 264, for example AD5934 commercially available from Analog Devices of Norwood, Mass., USA. Impedance converter 264 and/or processor 262 can be configured to synthesize a drive signal with drive circuitry 212 comprising direct digital synthesis (DDS) and digital to analog conversion (DAC). Impedance converter 262 and/or processor 262 can also be configured to measure the impedance signal with analog to digital conversion (ADC) and a digital Fourier transform (DFT). In many embodiments, processor 262 is connected to a precision oscillator, for example a know quartz 16 MHz oscillator, so as to provide an accurate and synchronous time base. The synchronous time base is provided for the drive signal and analog to digital conversion, such that time and/or phase delay of the circuitry and tissue impedance measurement can be accurately determined. Thus, the measured phase angle of a signal may correspond to the time delay from digitization of the drive signal at the DAC to measurement of the signal at the ADC. Work in relation to embodiments of the present invention suggests that time delays of the drive circuitry and time delays of the measurement circuitry can correspond to a phase angle of 270 degrees at some measurement frequencies, such that calibration that includes delays of the drive circuitry and measurement circuitry can provide improved accuracy of the determined complex tissue impedance.

The four wire, for four electrode, impedance determination uses that property that current through a series circuit will create a voltage drop across each component that is proportional to their respective impedances. The general form of this, realizing that each variable is a complex number, is:

$$Z_{unkown}/R_{cal} = V_u/V_r$$

which becomes $$Z_{unkown} = (V_u/V_r)R_{cal}$$

where $Z_{unknown}$ comprises the unkown impedance, or tissue impedance, $R_{cal}$ comprises the resistance of the calibration circuitry, $V_u$ comprises the voltage signal across the unknown impedance, and $V_r$, comprises the voltage across the calibration resistor.

Processor system 260 can be configured to make complex calibration and tissue impedance measurements at many frequencies as described above. In specific embodiments, processor system 262 can store a known value of the resistance of calibration circuitry in memory of the processor. For example, the calibration circuitry may comprise a known resistance, $R_{cal}$, that can be measured with an ohm meter and stored in processor memory as a real number. The processor system can select calibration circuitry 220 in a first configuration of at least one switch 230, as described above. A drive current is passed through calibration circuitry 220 and an impedance signal measured with measurement circuitry 250. The impedance signal is digitized with the analog to digital converter 256, for example with quadrature sampling for about 256 cycles corresponding to 1024 samples of the measurement calibration signal. Processor system 260, for example processor 262 and/or impedance converter 262, calculates a digital transform of the signal, for example at least one of a discrete Fourier transform (DFT), a cosine transform or a sine transform of the measurement signal. In a specific embodiment, processor 262 calculates a cosine transform of the measurement signal and a sine transform of the measurement signal at the tissue excitation frequency with the current. The cosine transform comprises a known transform and calculating the cosine transform of the measurement signal may comprise multiplying the measurement signal by the cosine of the phase of the drive signal at each sampled data point and summing the values. The sine transform comprises a known transform and calculating the sine transform of the measurement signal may comprise multiplying the measurement signal by the sine of the phase of the drive signal at each sampled data point and summing the values. The cosine transform of the measured impedance calibration signal, $C_c$, corresponds to the real component, or resistance, of the measured impedance calibration signal, and the sine transform of the measured impedance calibration signal, $C_s$, corresponds to the imaginary component, or reactance, of the measured impedance calibration signal.

The measured complex impedance calibration signal can be expressed as $$Z_{cal}=(C_c+jC_s)$$

The complex calibration coefficient, $Z_{coef}$, can be expressed as $$Z_{coef}=R_{cal}/Z_{cal}=R_{cal}/(C_c+jC_s)$$

As noted above, although the calibration circuit comprises a substantial resistance, often without a substantial reactance component, the complex calibration coefficient may include a substantial reactance component due to the phase and/or time delay of the drive circuitry, time delay of the measurement circuitry, and/or additional parasitic impedances such as the electrode to tissue coupling. The complex calibration coefficient can be used to calculate the tissue impedance, such that the phase and/or time delays can be calibrated out of the tissue impedance measurement along with the parasitic impedances such as the electrode to tissue coupling. Work in relation to embodiments of the present invention suggests that the phase delay due to the drive circuitry and/or measurement circuitry can be 90 degrees or more, for example 270 degrees, such that a much more accurate determination impedance can be made using the calibration circuitry and complex calibration coefficient.

The tissue can be selected for measurement with the at least one switch in the second configuration, as described above. A drive current can be passed through measurement electrodes with measurement circuitry 210 and a tissue impedance signal measured from the measurement electrodes with measurement circuitry 250. The tissue impedance signal is digitized and the cosine and sine transforms of the measured tissue impedance signal calculated. The cosine transform of the tissue measured tissue impedance signal, $T_e$, corresponds to the real component, or resistance, of the measured tissue impedance signal and the sine transform of the measured tissue impedance signal, $T_s$, corresponds to the imaginary component, or reactance, of the measured tissue impedance signal. The complex tissue impedance signal, $Z_{ts}$, can be expressed as $$Z_{ts}=T_c+jT_s$$

The complex impedance of the tissue, $Z_{tissue}$, can be determined and/or calculated in response to the complex impedance calibration signal and the complex tissue impedance signal. In specific embodiments, the complex impedance of the tissue can be calculated in response to the measured complex calibration coefficient and the measured complex tissue impedance signal by multiplying the measured complex calibration coefficient and the measured complex tissue impedance signal, expressed as $$Z_{tissue}=Z_{cal}*Z_{ts}=Z_{cal}*(T_1+jT_2)=[(T_1+jT_2)/(C_e+jC_s)]*R_{cal}$$

Therefore, the complex impedance of the tissue can be calculated in response to the measured calibration impedance signal and the measured tissue impedance signal, such that phase and/or time delays of the drive circuitry, measurement circuitry and/or parasitic impedance of tissue are corrected. In some embodiments, the complex impedance of the tissue can be determined from the complex ratio of the complex tissue impedance signal over the complex calibration impedance signal times the resistance of the calibration resistor. The changes in the current applied to the tissue with the drive circuitry and changes in the gain of the measurement circuitry can be corrected by repeating the above measurements and calculations at additional frequencies. As the impedance of the calibration circuitry, for example the calibration resistor, remains substantially constant at different measurement frequencies these additional measurements can provide very accurate measurements of tissue impedance at many frequencies.

Although the complex calibration impedance measurements and complex tissue impedance measurements are explained with reference to digital transforms, similar results can be obtained with known methods using lock-in detection and/or synchronous demodulation. In some embodiments, lock-in detection with first and second lock-in amplifiers can be driven at the measurement frequency, in which the first and second lock-in amplifiers are phase shifted by ninety degrees to obtain the real and imaginary components, respectively, of the measured impedance signal. A switch, as described above, can select the calibration circuitry or the tissue electrodes for measurement with the phase shifted lock-in amplifiers.

Figure 2B:
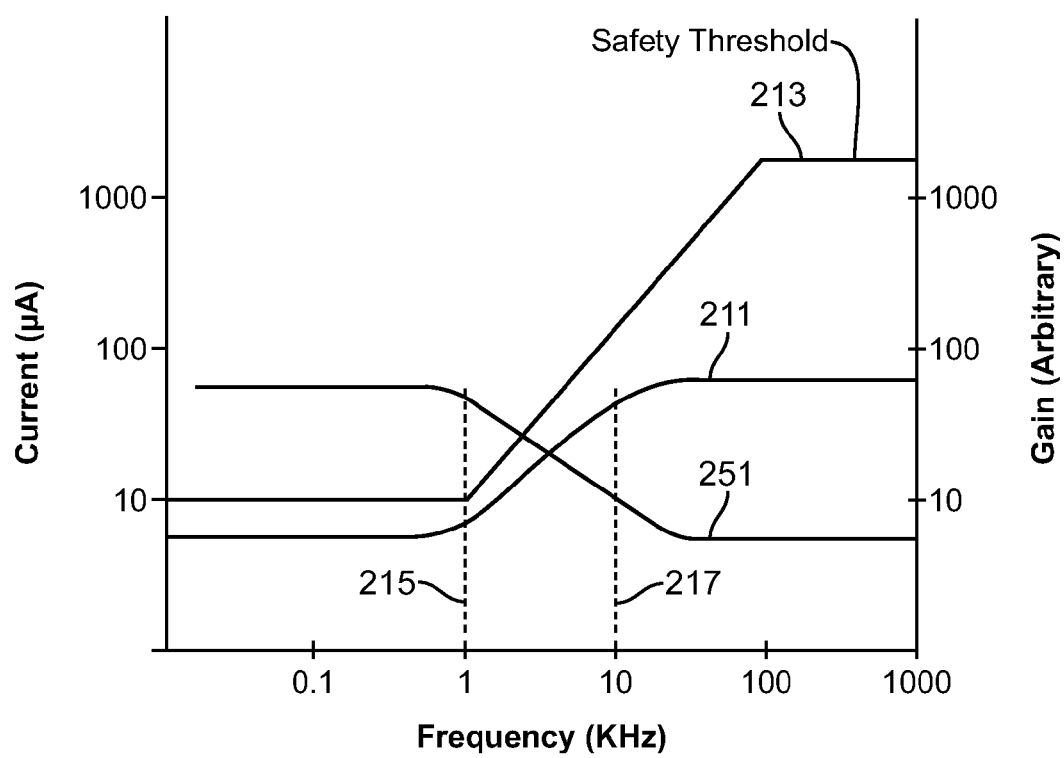
FIG. 2B shows an inverse frequency response of the drive circuitry and measurement circuitry, according to embodiments of the present invention.

FIG. 2B shows an inverse frequency response of the drive circuitry 210 and measurement circuitry 250. Drive circuitry 210 generates a drive current 211. Measurement circuitry 250 comprises a gain 251. A safety threshold 213 is shown that corresponds to known safe current requirements, for example AAMI ES1 requirements. Drive current 211 is below a safety threshold 213. Drive current 211, safety threshold 213 and gain 211 change with frequency. At a first frequency 215, for example about 1 kHz, safety threshold 213 corresponds to about 10 µA. Safety threshold 213 corresponds to about 10 µA for frequencies below 1 kHz. From about 1 kHz to about 100 kHz, threshold 213 increases by about 10 µA per decade from about 1 kHz to about 100 kHz. At frequencies above about 100 kHz, for example from 100 kHz to 1 MHz, safety threshold 213 comprises a safe currently limit of about 1000 µA or 1 mA. As drive current 211 increase from first frequency 211 to a second frequency 217, for example 10 kHz, drive current 213 increases substantially, for example about an order of magnitude, such that the drive current at the second frequency is above the safety threshold at the first frequency. As drive frequency 211 increases above 1 kHz, gain 251 of the measurement circuitry decreases. In specific embodiments, gain 251 is about 100 at first frequency 215 of about 1 kHz and gain 251 is about 10 at second frequency 217 of about 10 kHz. The total system gain of the impedance circuitry can be defined as the product of the drive current times the measurement circuitry. The inverse frequency response of the drive circuitry and measurement circuitry is such that the total system gain is substantially uniform, for example to within 25%, over from the first frequency to the second frequency, even though the drive current increase by at least a factor of two, for example by a factor of 10. Therefore, the impedance circuitry provides a substantially uniform total system gain when the drive current at higher frequency exceeds a safety threshold at the lower frequency.

Figure 3A:
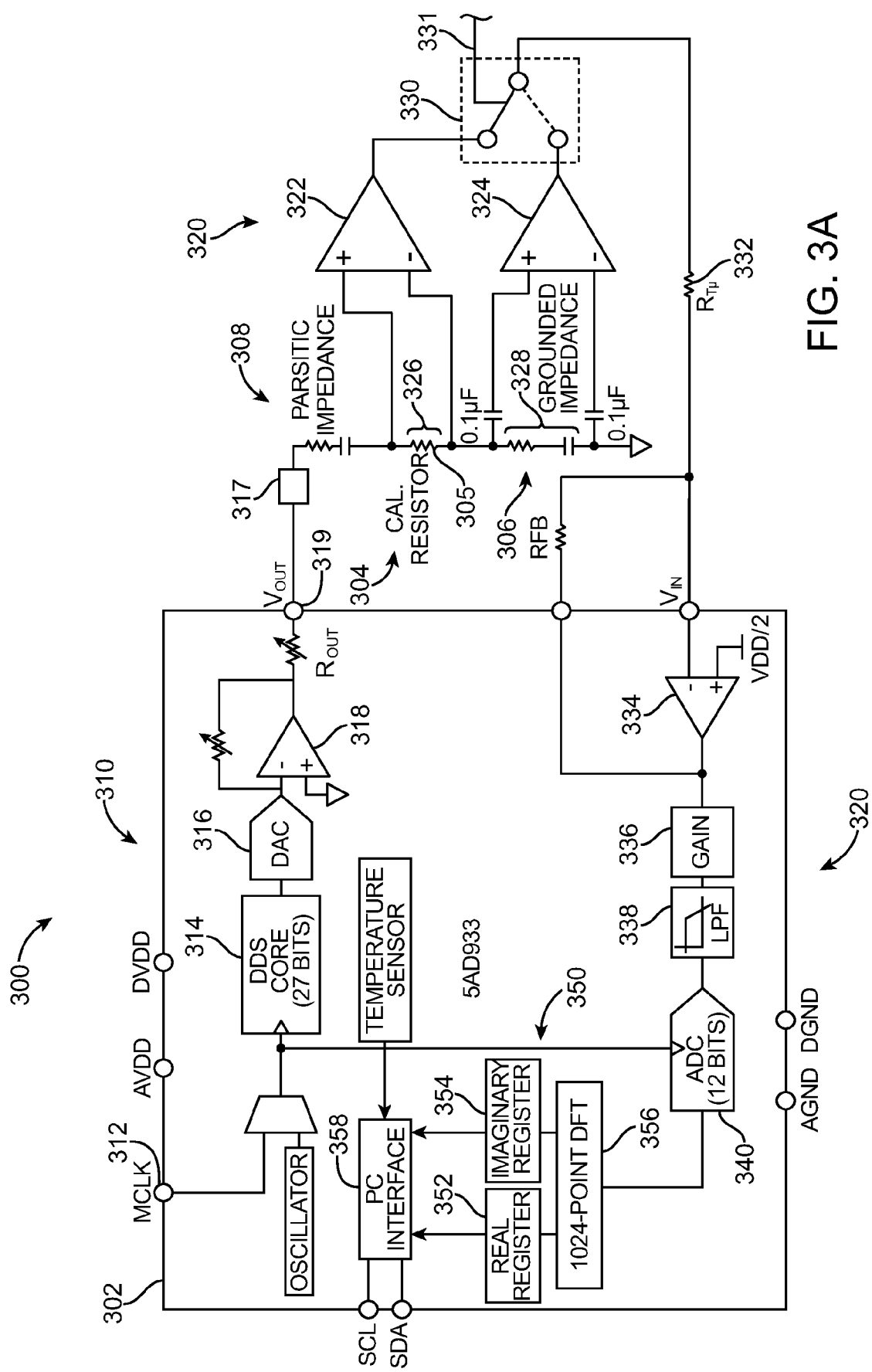
FIG. 3A shows circuitry for measuring patient impedance with an impedance converter, according to embodiments of the present invention.

FIG. 3A shows circuitry 300 for measuring patient impedance with an impedance converter, according to embodiments of the present invention. The impedance converter circuitry can be configured to determine tissue impedance with a four point measurement technique comprising a grounded unknown impedance and distributed parasitic impedance. In many embodiments, circuitry 300 comprises an impedance converter 302. Impedance converter 302 may comprise a known impedance converter, for example an Analog Devices AD5934 and/or AD5933. Circuitry 300 comprises drive circuitry 310, calibration circuitry 304, measurement circuitry 320 and processor circuitry 350. In many embodiments, measurement circuitry 300 can be used to separate the excitation signal from the measurement signal in the AD5934. In many embodiments, measurement of the impedance is grounded, such that any distributed parasitic impedance can be factored out.

Drive circuitry 310 may comprise a master clock signal 312, for example from a known 16 MHz oscillator. The oscillator and/or master clock are coupled to a digital data synthesis core, for example DDS core 314. DDS core 314 can generate a digital representation of a waveform. DDS core 314 is coupled to a digital to analog converter, for example DAC 316. An amplifier 318 is coupled to the output of DAC 316 to provide an excitation voltage at an output 319 of impedance converter 302. Output 317 can be connected to patient protection circuitry, for example network 317 that limits current to the patient in response to frequency, as described above. A parasitic impedance 308 can be distributed among components of circuitry 300 and may comprise capacitance from electrodes coupled to the patient, among other sources.

Calibration circuitry 304 may comprise a resistor 305. Current from the drive circuitry can pass a current through resistor 305 that can be measured to calibrate the system. Current through calibration circuitry 304 that comprises resistor 305 generates a calibration signal 326.

Measurement circuitry 320 comprises an amplifier 322, for example instrumentation amplifier, to measure voltage across resistor 305, such that the current through the resistor can be measured. Measurement circuitry 320 comprises an amplifier 324, for example an instrumentation amplifier, to measure a tissue impedance signal 328. Amplifier 322 and amplifier 324 are coupled to a switch 330. Switch 330 can select amplifier 322 or amplifier 324. A control signal 331 to switch 330 can select output of amplifier 322 or output of amplifier 324 for further processing with the impedance converter. In some embodiments, the output of amplifier 322 and the output of amplifier 324 can be measured in parallel, for example with two digital to analog converters on a processor. The output of switch 330 is coupled to a resistor 332 to convert the output voltage from the selected amplifier, either amplifier 322 or amplifier 324, to current that is measured with components of impedance converter 302. Impedance converter 302 may comprise components of measurement circuitry 320 such as an amplifier 334, a selectable gain 336, a low pass filter 338 and an analog to digital converter, for example ADC 340. Amplifier 334 comprises a current follower that converts an input current to a voltage. Selectable gain 336 may comprise switches to select a 1× or 5× gain from amplifier 334. Low pass filter 338 may comprise a known low pass filter to pass low frequencies and inhibit high frequencies. ADC 340 may comprise a known ADC with 12 bit resolution.

Circuitry 300 comprises processor circuitry 350, for example circuitry on an AD 5934 that processes signals from ADC 340. Processor circuitry 350 may comprise 1024-point DFT circuitry 356 to compute the discrete Fourier transform of the signal. In some embodiments, circuitry 300 can be configured to provide 1024 samples for 256 cycles at the selected excitation frequency, such that the data are sampled four times, or quadrature sampled, for each cycle at the measurement frequency. A real register 352 comprises memory that stores the real component of the 1024 point DFT from circuitry 356. An imaginary register 354 comprises memory that stores the imaginary component of the 1024 point DFT from circuitry 356. An interface 358 allows another device, such as microcontroller, to access the real and imaginary components written in memory. The real and imaginary components of the DFT can be processed to determine the tissue impedance in response to the DFT of calibration signal 326 and the DFT of the tissue impedance signal 328. The real and imaginary components of the DFT of calibration signal 326 may comprise a complex calibration signal, and the real and imaginary components of the DFT of the tissue impedance signal 328 may comprise a complex tissue signal. The impedance of the tissue can be determined by computing the complex ratio of the complex tissue signal over the complex calibration signal time and multiplying the complex ratio by the resistance of calibration resistor 305.

Impedance converter 302 may comprise as an synchronous exciter/voltmeter that drives a series connected combination of calibration resistor 305 and tissue impedance 306 and one or more parasitic impedances 308 with a substantially fixed voltage. To determine the tissue impedance, impedance converter 302 can be commanded to make two measurements, one across the calibration resistor 305, and one across the tissue impedance 306. Instrumentation amplifier inputs and/or outputs can be switched accordingly for each measurement with switch 330. Since substantially the same current flows through both components, the relative phasor voltage across each is proportional to the impedance. A current sensing component may comprise calibration resistor 305 so as to give a reference phase angle of zero degrees. By simply computing the complex ratio of the real and imaginary components of complex tissue signal over the real and imaginary components of the complex calibration signal, and multiplying by the resistance value of resistor 305, the complex tissue impedance can be determined. In some embodiments, the excitation voltage may be replaced with a controlled excitation current such that measurement of voltage across the calibration resistor can be replaced with the constant current. This constant current method may use a complex energy efficient bipolar voltage to current converter. The constant voltage method and constant drive current can factor out distributed parasitic impedances, since the impedances are in series and current is consistent through all the impedances. In addition to the benefits described above, these methods easily allow one side of the load to be at either DC or AC ground and do not require a finite DC resistance return path.

Figure 3B:
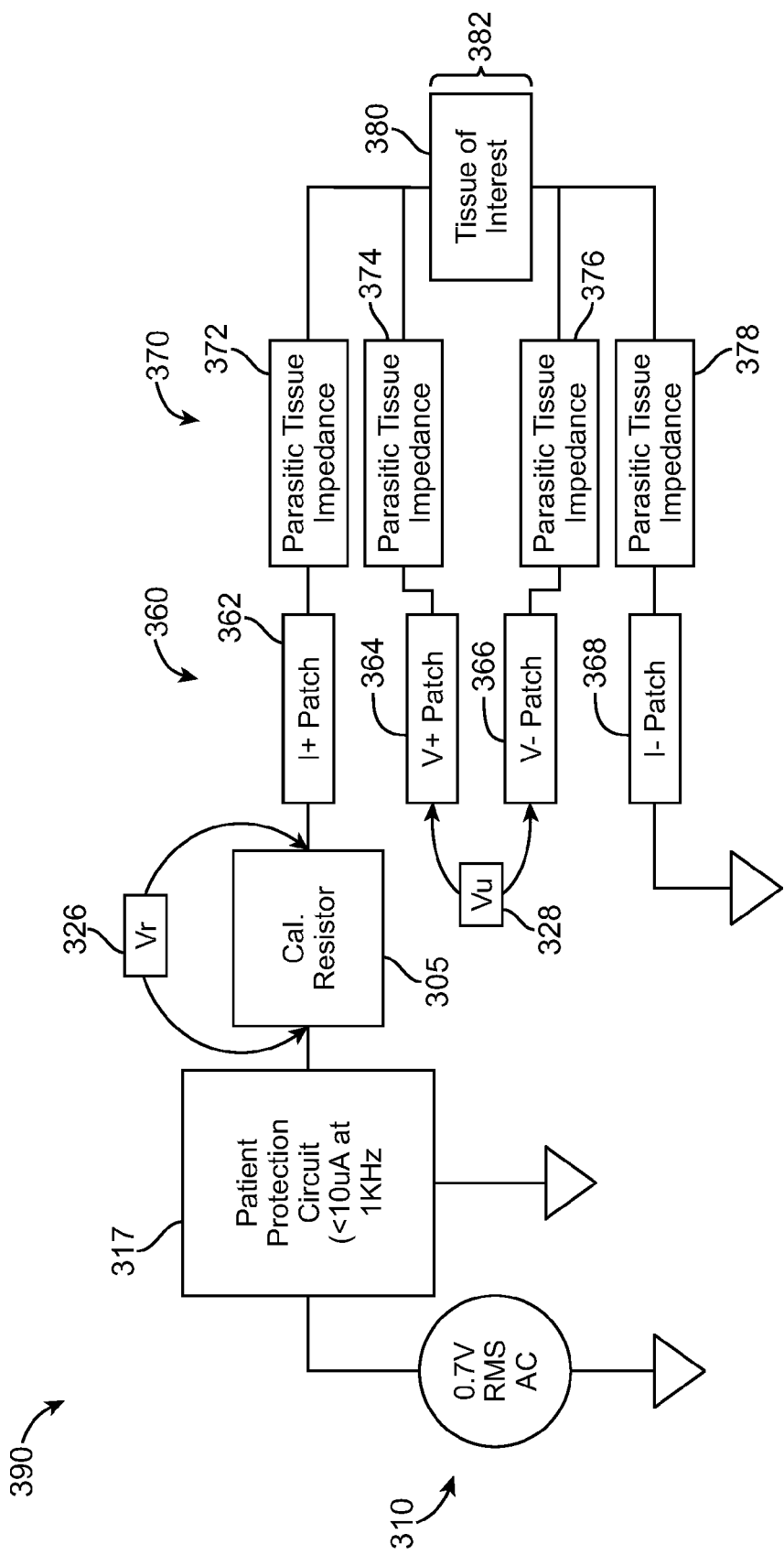
FIG. 3B shows a model for measuring patient impedance with circuitry as in FIG. 3A.

FIG. 3B shows an equivalent circuit 390 that may comprise a model for measuring tissue impedance with circuitry 300 that shows components that contribute to the impedance measurements. Drive circuitry 310 and network 317 pass the drive current through the calibration circuitry comprising calibration resistor 305. Calibration impedance signal 326 corresponds to a voltage across the resistor. At least four electrodes that can couple the patient tissue to the circuit include electrode 362, electrode 364, electrode 366 and electrode 368. Electrode 362 and electrode 368 may comprise at least two drive electrodes to pass current through the tissue. Electrode 364 and electrode 366 may comprise at least two measurement electrodes. Tissue impedance signal 328 may correspond to a voltage measured between the at least two measurement electrodes comprising electrode 364 and electrode 366. At least four parasitic tissue impedances comprise parasitic impedance 372, parasitic impedance 374, parasitic impedance 376, and parasitic impedance 378. A tissue of interest 380 may comprise a tissue below the skin of the patient, for which tissue hydration can be determined based on the impedance. The drive current passed through electrode 632 and electrode 368 generates a voltage signal 382 across tissue of interest 380.

Measurement of the impedance of tissue of interest 380 can be affected by a significant number of uncontrolled series impedances, such as the at least four parasitic impedances. In addition, patient protection circuit comprising network 317 that limits maximum applied current as a function of frequency introduces a frequency dependent excitation voltage and may also introduce a non-zero equivalent series impedance. In many embodiments, an assumption about circuit 390 may comprise that $V_u$ is measured by a very high input impedance amplifier, for example an instrumentation amplifier, so that any sensing channel parasitic series impedance is negligible in comparison.

Figure 3C:
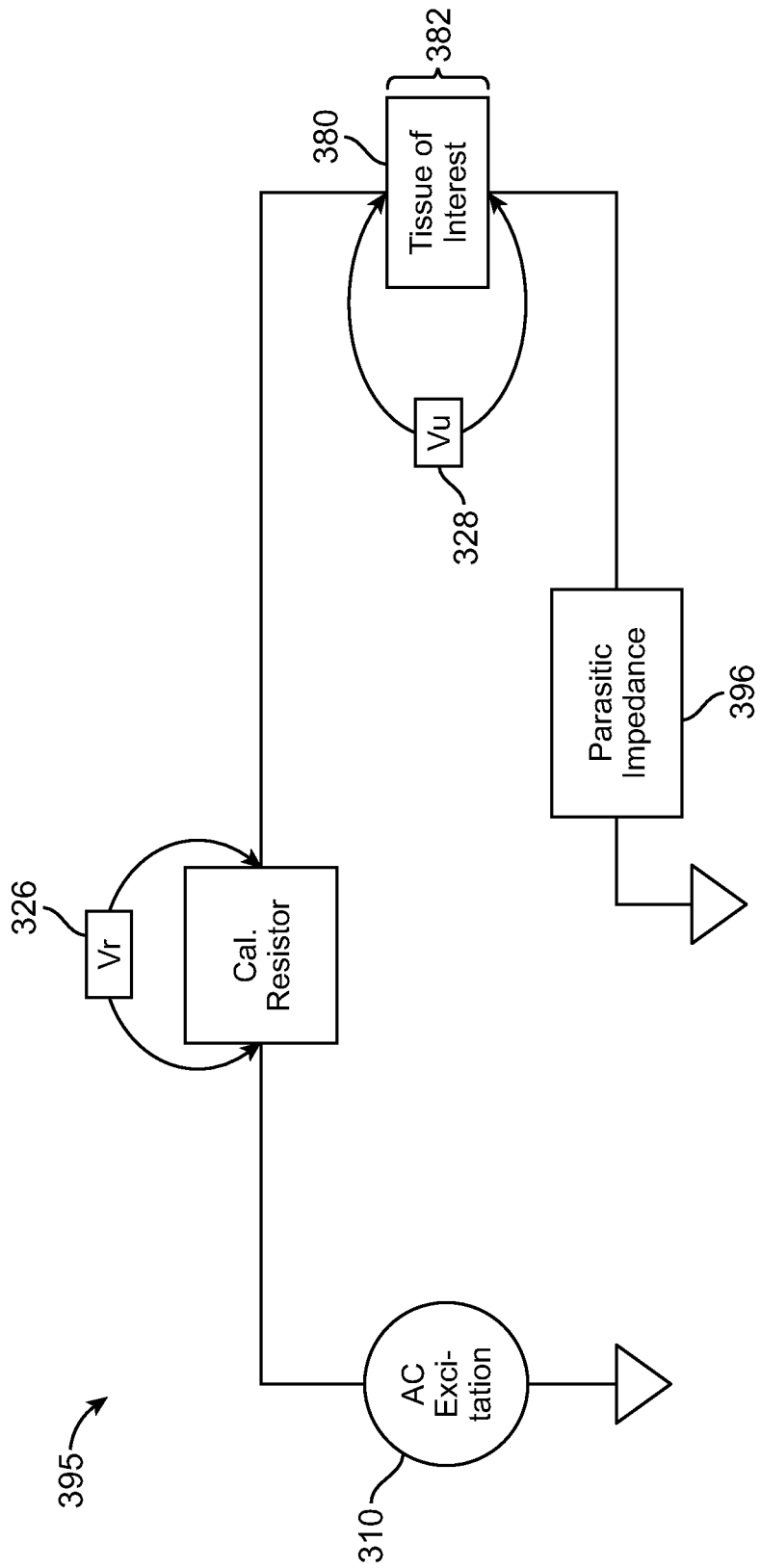
FIG. 3C shows a model equivalent to the model of FIG. 3B that allows for correction of parasitic impedance, according to embodiments of the present invention.

FIG. 3C shows an equivalent circuit 395 of a model that is similar to the model of FIG. 3B and allows for correction of parasitic impedance. For analysis simplification, many of the parasitic impedances of FIG. 3B can be lumped into a single value of lumped parasitic impedance 396. With this method, the tissue impedance signal 328 may more closely correspond to the voltage signal 382 across tissue of interest 380. Equivalent circuit 395 shows lumped parasitic impedance 396 connected to ground, although the lumped parasitic impedance can be disposed anywhere in the series circuit as needed during analysis, for example to determine worst case operating conditions. In many embodiments, one can assume that the excitation voltage corresponding to the drive current is whatever voltage is available between ground and the high-side of the calibration resistor.

When making $V_r$ and $V_u$ differential voltage measurements with the instrumentation amplifiers, a significant common mode component of the excitation signal may be present at the instrumentation amplifier input. Known instrumentation amplifiers with high common mode rejection ratios, and appropriate known models can be used to select the instrumentation amplifiers in the measurement circuitry.

The four point, or four electrode, method of measuring voltage across the series connected calibration resistor and series connected tissue impedance produces a maximum analog to digital conversion signal when the unknown impedance is large. The largest calibration resistor voltage, $V_r$, may occur when the unknown tissue impedance is zero ohms. The value of calibration resistor can be chosen during design, so that saturation of the calibration signal and tissue measurement signal does not occur. The tissue impedance can be from about 50 to 100 ohms. The calibration resistance may be about twice the maximum tissue impedance, for example about 200 ohms. The measurable limits of impedance, the impedance resolution limits, the gains of each of the impedance converter and instrumentation amplifier stages and the effects of parasitic impedance on measurement limits can be calculated using known engineering analysis techniques to determine an optimal configuration of the circuitry components for resolution and dynamic range.

Figure 4:
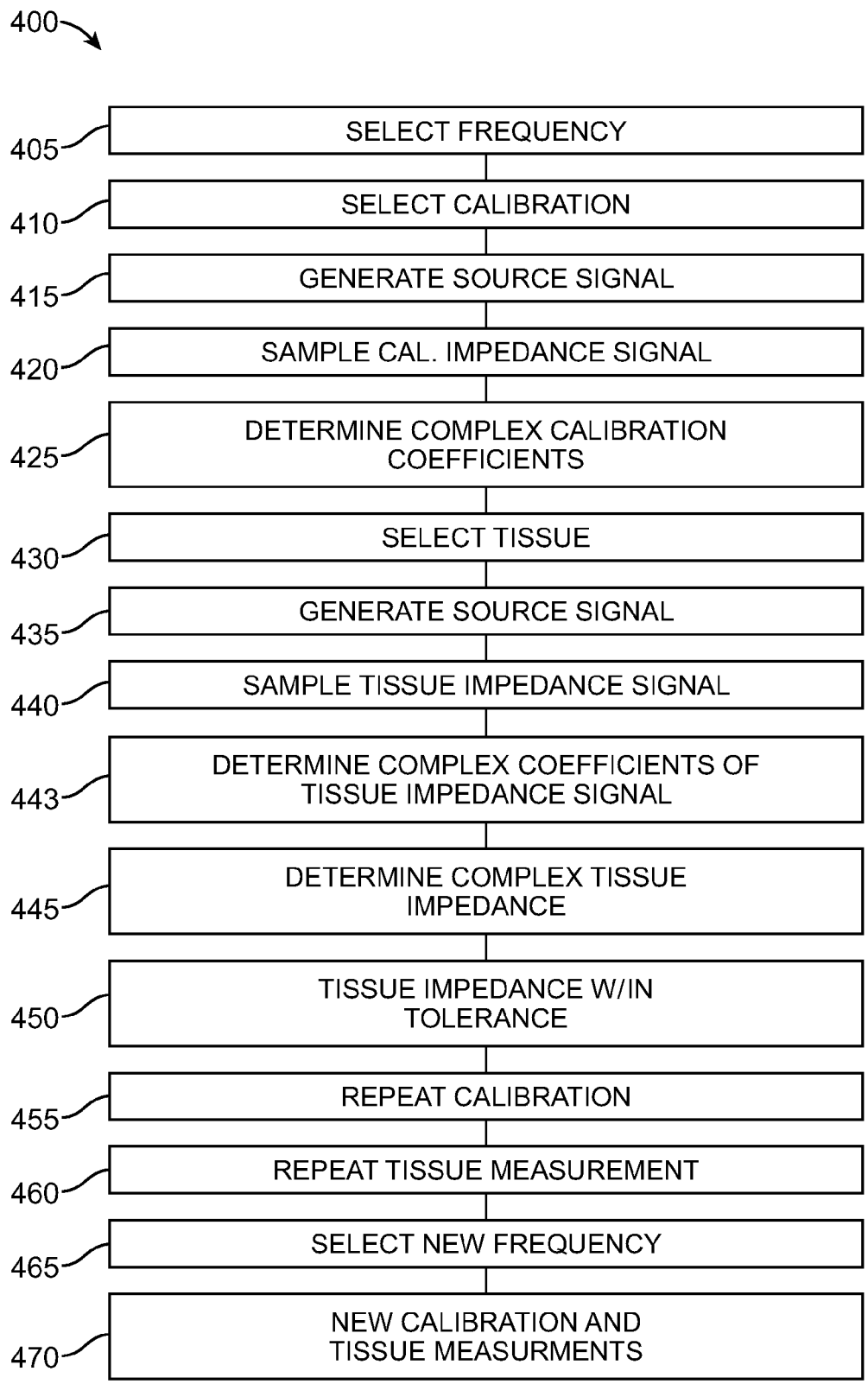
FIG. 4 shows a method of measuring patient impedance, according to embodiments of the present invention.

FIG. 4 shows a method 400 of measuring patient impedance. Method 400 can be implemented with the impedance converter, processor and/or circuits shown above. In specific embodiments, the processor comprises a tangible medium configured to perform method 400. A step 405 selects a frequency. The selected frequency is within a range from about DC to about 1 Mhz, and can be from about 100 Hz to about 100 kHz.

A step 410 selects calibration, for example by configuring switches coupled to the drive circuitry and measurement circuitry, such that the calibration circuitry is measurement with the drive circuitry and measurement circuitry. The calibration circuitry can be selected with switches such that on board calibration circuitry located on the measurement device is selected. The calibration circuitry may comprise a resistor, such that the selected calibration circuitry substantially comprises a resistance with very little reactance. The resistance of the calibration circuitry may comprises a known resistance, for example a DC resistance from a resistor, that is used as a calibration value stored on the processor and/or impedance converter. A step 415 generates a source signal. The source signal is generated at the selected frequency. The source signal generally comprises a time base that is synchronous with the digitization/detection circuitry to determine both amplitude and phase of the measurement signal. A step 420 samples the impedance signal such that the calibration circuitry is measured at the selected frequency. The drive electronics, measurement electronics and time delay, for example phase lag, of the system electronics are calibrated with the selected frequency. As the calibration circuitry substantially comprises a resistance, most of the phase of the measured calibration signal can be attributed to delays in the drive circuitry and the measurement circuitry. The impedance signal sampled from the resistance circuitry can be digitized with an A/D converter and may comprise quadrature sampling of about 1024 data points at the selected frequency for about 256 full cycles. The cosine and sine transforms of the impedance signal can be calculated to determine the complex impedance of the calibration signal. The complex impedance of the calibration signal can then be multiplied and/or divided by the known calibration value, for example known impedance of the calibration resistor, to determine the real and imaginary components of the complex calibration coefficient. A step 425 determines the complex calibration coefficients. The complex calibration coefficients generally comprise a magnitude that corresponds to the resistance of the calibration circuitry and a phase that corresponds to delays in the drive circuitry and measurement circuitry.

A step 430 selects tissue, for example by configuring the switches coupled to the drive circuitry and measurement circuitry, such that an outer two of the at least four electrodes are coupled to the drive circuitry to pass current through the tissue and an inner two, or remaining two, of the at least four electrodes are coupled to the measurement circuitry to measure an impedance signal from the tissue. A step 440 samples the impedance of the tissue. The impedance signal from the sampled tissue can be digitized with an A/D converter and may comprise quadrature sampling of about 1024 data points at the selected frequency for about 256 full cycles. The cosine and sine transforms of the impedance signal can be calculated to determine the complex impedance of the tissue signal. The complex impedance of the tissue signal can then be multiplied and/or divided by the complex calibration coefficients to determine the impedance of the tissue. This use of complex impedance calibration coefficients, based on a known resistance in the calibration circuitry, can cause inaccuracies of the gain and phase of the drive and measurement circuitry to drop out of the calculated tissue impedance, such that the determined tissue impedance corresponds to the actual impedance of the tissue. A step 445 determines the tissue impedance in response to the complex impedance calibration coefficients and the complex impedance of the tissue signal, for example with complex multiplication.

A step 450 determines whether the tissue impedance is within a calibration tolerance. For example, the processor may check to determine whether the tissue impedance is within 20% of the calibration circuitry and/or within 20% of a previous tissue measurement. A step 455 repeats calibration. Calibration can be repeated with the calibration circuitry, as described above, for example in response to the tissue measurement outside the tolerance range. A step 460 repeats the tissue measurement. The tissue measurement may be repeated when the calibration step is repeated.

A step 465 selects a new frequency, for example a second frequency greater than the first frequency. In many embodiments, the amount of injected current will increase above a safety threshold of the current injected at the first frequency, and the gain will decrease, for example with an inverse frequency response, such that the signal remains within the range of the A/D converter. New calibration and tissue measurements are taken at the new frequency. The impedance signal of the calibration circuitry can be measured at the new frequency to determine the complex calibration coefficients, as described above, at the second frequency. One will appreciate that a resistor will have a substantially fixed resistance at the new frequencies, such that the resistance, for example the real calibration value, of the calibration circuitry may be the same at the second frequency as the first frequency. Therefore, changes in the measured calibration signal can be substantially attributed to changes in the drive current of the drive circuitry and/or gain and time delay measurement circuitry. The tissue impedance signal at the new frequency can be determined with the complex calibration coefficient and complex tissue signal. Steps 465 and 470 can be repeated to measure impedance and hydration at many frequencies.

It should be appreciated that the specific steps illustrated in FIG. 4 provide a particular method of measuring impedance of a patient, according to an embodiment of the present invention. Other sequences of steps may also be performed according to alternative embodiments. For example, alternative embodiments of the present invention may perform the steps outlined above in a different order. Moreover, the individual steps illustrated in FIG. 4 may include multiple sub-steps that may be performed in various sequences as appropriate to the individual step. Furthermore, additional steps may be added or removed depending on the particular applications. One of ordinary skill in the art would recognize many variations, modifications, and alternatives. For example, although the processor system and circuitry, as described above, can perform the method 400, additional analog circuits may be used, for example lock-in detection and synchronous demodulation circuits.

While the exemplary embodiments have been described in some detail, by way of example and for clarity of understanding, those of skill in the art will recognize that a variety of modifications, adaptations, and changes may be employed. Hence, the scope of the present invention should be limited solely by the appended claims.

What is claimed is:

1. A device for measuring an impedance of a tissue of a patient, the device comprising:
   an adhesive patch that includes at least four electrodes configured to couple to the tissue of the patient, the at least four electrodes comprising two measurement electrodes and two drive electrodes; and
   an electronics module comprising circuitry coupled to the at least four electrodes, the circuitry including drive circuitry coupled to the two drive electrodes to pass a current through the two drive electrodes, and sensing circuitry coupled to the two measurement electrodes to measure a signal generated across the two measurement electrodes as a result of the current through the drive electrodes, and a processor programmed to receive and process the signal measured from the two measurement electrodes to determine a tissue impedance of the patient;
   wherein the adhesive patch and the electronics module are separable.

2. The device of claim 1, wherein the adhesive patch can be replaced and the electronics module reused with multiple adhesive patches.

3. The device of claim 1, wherein the electronics module further comprises a printed circuit board on which at least some of the electronics are mounted.

4. The device of claim 3, wherein the printed circuit board is a flex printed circuit board.

5. The device of claim 4, wherein the electronics module further comprises:
   an electronics housing;
   a battery; and
   a cover over the electronics housing, battery, and flex printed circuit board.

6. The device of claim 1, further comprising a flexible, breathable cover over the electronics module.

7. The device of claim 1, further comprising wireless communications circuitry that transmits data to a remote server.

8. The device of claim 1, wherein the device takes impedance readings periodically, and wherein the electronic module further comprises a memory of sufficient size to hold impedance readings accumulated over a period of 90 days or more.

9. The device of claim 1, wherein the electronics module further comprises electrocardiogram circuitry coupled to two or more of the at least four electrodes, the electrocardiogram circuitry configured to measure an electrocardiogram signal of the patient.

10. A system, comprising:
    an adherent device for measuring an impedance of a tissue of a patient, the adherent device comprising 1) an adhesive patch that includes at least four electrodes configured to couple to the tissue of the patient, the at least four electrodes comprising two measurement electrodes and two drive electrodes; and 2) an electronics module comprising circuitry coupled to the at least four electrodes, the circuitry including drive circuitry coupled to the two drive electrodes to pass a current through the two drive electrodes, and sensing circuitry coupled to the two measurement electrodes to measure a signal generated across the two measurement electrodes as a result of the current through the drive electrodes, a processor programmed to receive and process the signal measured from the two measurement electrodes to determine a tissue impedance of the patient, and wireless communication circuitry that transmits data, wherein the adhesive patch and the electronics module are separable; and an intermediate device having circuitry that wirelessly receives data transmitted via the wireless communication circuitry from the adherent device and forwards the data to a remote server.

11. The system of claim 10, wherein the electronics module further comprises a rechargeable battery.

12. The system of claim 11, wherein the intermediate device includes a battery charger, and wherein the electronics module can be removed from the adhesive patch and coupled to the intermediate device to charge the rechargeable battery.

13. A method of monitoring a patient, the method comprising:

adhering an adherent device to a skin of the patient, the adherent device comprising 1) an adhesive patch that includes at least four electrodes configured to couple to the tissue of the patient, the at least four electrodes comprising two measurement electrodes and two drive electrodes; and 2) an electronics module comprising circuitry coupled to the at least four electrodes, the circuitry including drive circuitry coupled to the two drive electrodes to pass a current through the two drive electrodes, and sensing circuitry coupled to the two measurement electrodes to measure a signal generated across the two measurement electrodes as a result of the current through the drive electrodes, and a processor programmed to receive and process the signal measured from the two measurement electrodes to determine a tissue impedance of the patient;

monitoring the patient for a period of time using the adherent device; and separating the electronics module from the adhesive patch.

14. The method of claim 13, wherein the electronics module is a first electronics module, the method further comprising:

replacing the electronics module with a second electronics module; and resuming monitoring of the patient.

15. The method of claim 14, wherein the first electronics module further comprises a rechargeable battery, the method further comprising charging the rechargeable battery.

16. The method of claim 13, wherein the adhesive patch is a first adhesive patch, the method further comprising:

removing the adhesive patch from the skin of the patient;

replacing the adhesive patch with a second adhesive patch;

coupling the electronics module to the second adhesive patch; and resuming monitoring of the patient.

17. The method of claim 16, further comprising accumulating measurements derived from the tissue impedance in a memory in the electronics module, the accumulated measurements including measurements taken using the first adhesive patch and measurements taken using the second adhesive patch.

18. The method of claim 13, wherein the electronics module comprises a calibration impedance, and wherein the method further comprises:

measuring the complex impedance of the calibration impedance;

measuring the complex impedance of the patient tissue; and correcting the measured complex impedance of the patient tissue using the measured complex impedance of the calibration impedance.

19. The method of claim 18, further comprising generating both hydration data and respiration data from the tissue impedance.

20. The method of claim 13, wherein the electronics module comprises electrocardiogram circuitry, and wherein the method further comprises:

coupling the electrocardiogram circuitry to two or more of the at least four electrodes; and measuring an electrocardiogram signal of the patient using the electrocardiogram circuitry.

21. The device of claim 1, further comprising calibration circuitry that includes a calibration impedance, wherein:

the drive circuitry is configured to pass current through the tissue and the calibration impedance simultaneously;

the sensing circuitry is configured to couple to the calibration circuitry to measure a calibration signal from the calibration impedance; and the processor is further programmed to receive the calibration signal and to determine the tissue impedance of the patient based in part on the calibration signal.

* * * * *